(12) United States Patent
Urakami et al.

(10) Patent No.: US 8,105,839 B2
(45) Date of Patent: Jan. 31, 2012

(54) DIAGNOSTIC KIT FOR ALZHEIMER'S DISEASE, DIAGNOSTIC MARKER, AND DETECTION METHOD FOR INDICATOR OF PATHOLOGICAL STATE THEREOF

(75) Inventors: Katsuya Urakami, Yonago (JP); Miyako Kimura, Yonago (JP)

(73) Assignee: National University Corporation Tottori University, Tottori (JP)

( * ) Notice: Subject to any disclaimer, the term of this patent is extended or adjusted under 35 U.S.C. 154(b) by 171 days.

(21) Appl. No.: 12/440,094

(22) PCT Filed: Sep. 6, 2007

(86) PCT No.: PCT/JP2007/067428
§ 371 (c)(1),
(2), (4) Date: Aug. 24, 2009

(87) PCT Pub. No.: WO2008/029886
PCT Pub. Date: Mar. 13, 2008

(65) Prior Publication Data
US 2011/0065197 A1   Mar. 17, 2011

(30) Foreign Application Priority Data
Sep. 6, 2006 (JP) ................................ 2006-242044

(51) Int. Cl.
G01N 33/68 (2006.01)
G01N 33/00 (2006.01)
C07K 14/42 (2006.01)
C07K 14/79 (2006.01)
C07K 16/00 (2006.01)
C40B 40/10 (2006.01)

(52) U.S. Cl. .............................. 436/86; 422/430; 422/50

(58) Field of Classification Search ................ 436/86; 422/430, 50
See application file for complete search history.

(56) References Cited

OTHER PUBLICATIONS

Urakami, K., Identification of WGA-Coupled Glycoprotein as Alzheimer's Disease Diagnostic Marker and Establishment of Inspection Method, English Translation obtain Apr. 2011, Health & Labor Fund Assigned Study Reports, pp. 20-28.*
International Search Report for PCT/JP2007/067428.
Katsuya Ura Gami, "Alzhe i mer-byo S hindan Marker A to Shite no WGA Ketsugo Totanpaku no D ote i to Kensa Hoho no Kakurutsu", Kosei Rod o Kagaku Kenkyuhi Hojokin Choju Kagaku S ogo Kenkyu J igyo Chiho no Screening Oyobi S oki S hindanho no Kakurutsu ni Kansuru Rinsho Kenkyu Kenkyu He ise i 16 to 17 Nend o Sogo Kenkyu Hokokus ho, Mar. 2006, pp. 20 to 28.
Susan J.Van Rensburg,et al., 5- and 6-g lyc osylati on of transferr in in patients with Alzheimer's disease., Metabolic Brain Disease, 2004, p. 89-96, vol. 19 No. 1/2, Plenum Publishing Corporation, New York.
Han-Ling Yu, et al., Aberrant profiles of native and oxidized glycoproteins in Alzheimer plasma., proteomics, 2003, p. 2240-2248, vol. 3 No. 11,Wiley-VCH Verlag GmbH & Co. KGaA, Weinheim.

(Continued)

*Primary Examiner* — Christine T Mui
(74) *Attorney, Agent, or Firm* — Pearne & Gordon LLP

(57) ABSTRACT

While the differential diagnosis of Alzheimer's disease as distinguished from other types of dementia and the diagnosis of Alzheimer's disease at an early stage where neuronal apoptosis has not proceeded yet are important for the treatment of Alzheimer's disease, it is difficult to differentially diagnose Alzheimer's disease at early stage via a diagnosis mainly made by questioning by a doctor or a diagnostic technique using phosphorylated tau or amyloid β-protein as an indicator. Accordingly, the development of a novel diagnostic technique has been desired. Thus, according to the present invention, by focusing on a transferrin having a sugar chain attached thereto, a diagnostic kit, a diagnostic marker, and a detection means for differentially diagnosing the disease condition of Alzheimer's disease at an early stage are provided.

19 Claims, 8 Drawing Sheets

OTHER PUBLICATIONS

S.J.Van Rensburg, et al., Glycosylation of transferrin in Alzheimer's disease and alcoholinduced dementia., Metabolic Brain Disease, 2000, p. 243-247, vol. 15 No. 4, Plenum Publishing Corporation, New York.

Lisa R. Fodero, et al.Wheat germ agglutinin-binding glycoproteins are decreased in Alzheimer's disease cerebrospinal fluid., Journal of Neurochemistry, 2001, p. 1022-1026, vol. 79,Wiley-VCH Verlag GmbH & Co. KGaA, Weinheim.

* cited by examiner

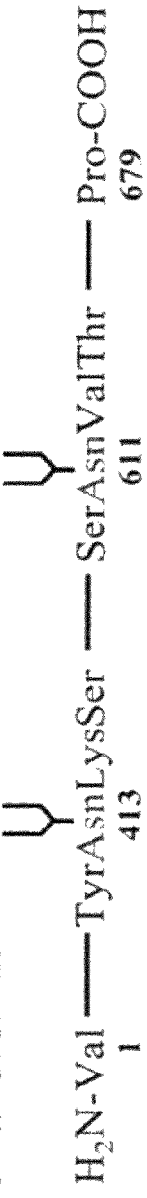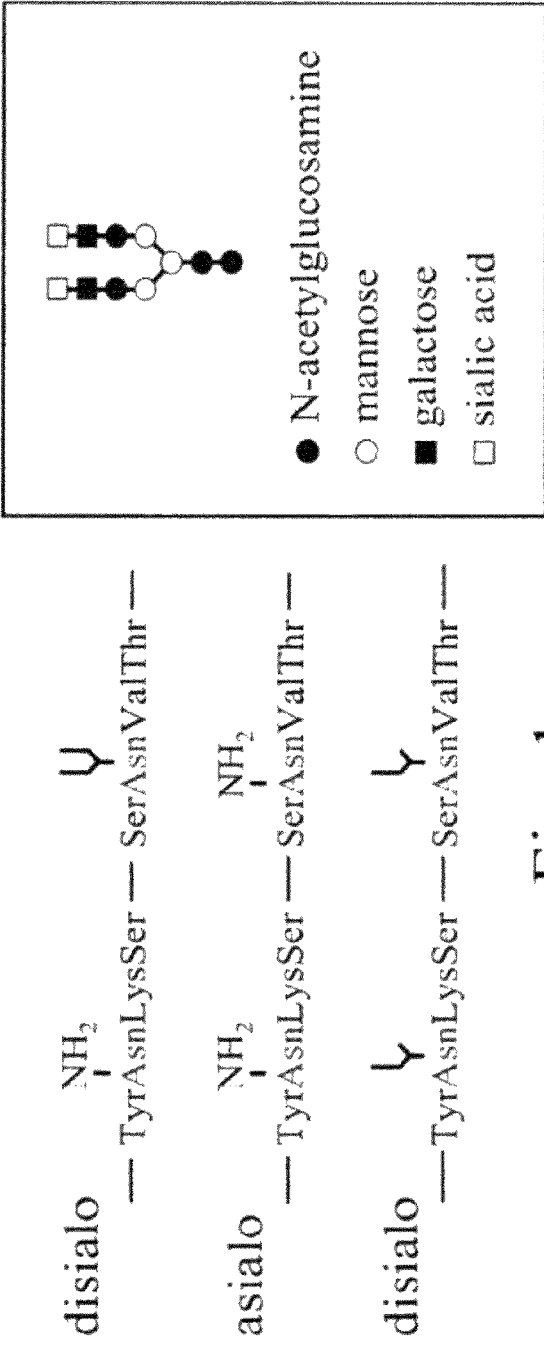
Fig. 1

Fig. 3  WGA Reactive Glycoproteins in Cerebrospinal Fluid

Fig. 5  (a) SDS-PAGE; (b) WGA Blotting; and
(c) Isoelectric Focusing of Transferrin in Cerebrospinal Fluid

DIAGNOSTIC KIT FOR ALZHEIMER'S DISEASE, DIAGNOSTIC MARKER, AND DETECTION METHOD FOR INDICATOR OF PATHOLOGICAL STATE THEREOF

TECHNICAL FIELD

The present invention relates to a diagnostic kit for Alzheimer's disease, a diagnostic marker, and a detection method for an indicator of a pathological state thereof.

BACKGROUND ART

Recently, along with the aging population in Japan, senile dementia has become a significant social problem. Currently, one out of every ten people over the age of sixty-five has dementia, and the number of senior citizens who are cognitively impaired is expected to rise from the current level of 1.3 million to 3.0 million by the year of 2035. Although the majority of those with dementia have multi-infarct dementia and Alzheimer's disease (AD), approximately one-half of the abovementioned people have Alzheimer's disease. The former has been effectively coped with using medical countermeasures, such as blood pressure control or relapse prophylaxis. However, the cause of Alzheimer's disease, a therapeutic method, and a preventive method therefor are still unclear, and thus immediate medical solutions are being sought. Moreover, with regard to types of dementia other than Alzheimer's disease, in addition to the abovementioned multi-infarct dementia, other forms of dementia specifically referred to as tauopathies also exist (e.g., frontotemporal dementia, dementia with Lewy Bodies, cortico-basal degeneration, and progressive supranuclear palsy), and since the symptoms of these are similar to those of Alzheimer's disease, clinically differentiating these diseases from Alzheimer's disease is difficult. However, if Alzheimer's disease can be differentially diagnosed by being differentiated from other types of dementia before the symptoms of dementia become an impediment, the establishment of an early diagnostic method for Alzheimer's disease is imperative, in order for recently tested therapeutic methods to be started even earlier, and for the progression of dementia to be slowed.

In Alzheimer's patients, atrophy of the cerebral cortex is seen, and pathologically, in addition to a high degree of neuronal loss, characteristic lesions such as neurofibrillary tangles or senile plagues are observed. Among these, senile plague is thought to be the earliest manifested and most significant change in Alzheimer's disease out of the characteristic changes thereof. The major component of senile plague is amyloid β-protein (Aβ), and since there are mutations in β-amyloid precursor protein (βAPP), which is an Aβ precursor gene in familial Alzheimer's disease showing autosomal dominant inheritance, the abnormal degradation or production of Aβ is thought to be strongly related to the pathogenesis and progress of Alzheimer's disease. Aβ is generated by being sequentially cleaved from β-amyloid precursor protein by β-secretase and γ-secretase (presenilin complex), a type of aspartic protease.

As a therapeutic agent for Alzheimer's disease, the insufficient acetylcholine compensatory effects of acetylcholinesterase inhibitors and the like are known. However, various signal transduction targeting agents that are based on the abovementioned mechanism are also being developed.

Diagnosis of Alzheimer's disease (senile dementia of Alzheimer's type) is clinically performed based on whether various diagnostic standards have been satisfied. In order to accomplish this, a detailed medical history is taken and various medical tests are performed, such as a functional neuroimaging test, a physiological test, a neuropsychological test, and an examination of clinical symptoms. However, in the early stages of Alzheimer's disease there are almost no specific abnormal findings upon examination, and therefore a high amount of reliance is currently placed on the medical specialist to perform the required exclusive diagnosis via detailed medical interviews and examinations of said person and his/her family. Actually, although symptoms such as personality changes, difficulty with the pronunciation of words, memory loss, forgetting the location of items, and forgetting names are seen in early stage Alzheimer's disease, accurately distinguishing the pathological "memory impairment" of early stage Alzheimer's disease from memory impairment due to aging (age-associated memory impairment) is extremely difficult. This also complicates the early detection of Alzheimer's disease, and thus is a major problem.

Moreover, during the early stages, it is thought that a physiological diagnostic marker capable of detecting Alzheimer's disease simply and reliably would be most effective for the objective of screening a large number of people. If early diagnosis or preclinical diagnosis becomes possible by the confirmation a diagnostic marker for Alzheimer's disease, it will allow for the planning of a treatment therapy or the administration of medication based on the confirmed diagnosis thereof, as well as open up new avenues in the prevention of Alzheimer's disease. At the same time, this type of early diagnosis also allows for the high costs required for the care and medical treatment of Alzheimer's patients to be prevented. Thus, the development and invention of a diagnostic marker capable of simply and easily detecting Alzheimer's disease has been strongly desired.

The diagnostic marker, in addition to reflecting the clinical state of Alzheimer's disease, should be both highly sensitive and highly specific to the detection of Alzheimer's disease. Various diagnostic products have so far been proposed from a large number of foreign and domestic groups as diagnostic markers for Alzheimer's disease. For example, the measurements of amyloid β-protein, glycosylated acetylcholine esterase, interleukin-6, substance P, cystatin C, serum apolipoprotein, serum homocysteine, APP isoform, interleukin 6, α1-antichymotrypsin (ACT), oxygenase-1, 24S-hydroxycholesterol, acetylcholine, somatostatin, vasopressin, wheat germ agglutinin (WGA) binding protein, acetylcholine transferase activity, acetylcholine esterase activity, and the like, have been proposed as diagnostic markers for Alzheimer's disease.

Non-patent document 1 discloses the quantitative variations in WGA binding proteins of Alzheimer's disease. Moreover, in non-patent document 2, the glycosylation of transferase and Alzheimer's disease are reviewed.

However, the relationship between the majority of these well-reported diagnostic markers and physiological changes is unclear, and the diagnostic values thereof are not necessarily defined. At present, as diagnostic markers that have been acknowledged as demonstrating clinical efficacy, only two are known, cerebrospinal fluid tau protein and amyloid β42.

Tau protein is the causative agent of a physiological change in which neurofibrillary tangles occur in the brains of Alzheimer's patients. In Alzheimer's disease, there is an increase in phosphorylated tau protein (or overall tau protein) in the cerebrospinal fluid, and thus measuring this tau protein is helpful in the diagnosis of Alzheimer's disease.

The amyloid β-protein employed as the diagnostic marker is an amyloid beta-peptide consisting of 42 amino acids, and the causative agent of a physiological change in which senile plague occurs in the brains of Alzheimer's patients. Since senile plague is manifested by the aggregation of amyloid β-protein in the brains of Alzheimer's patients, the cerebrospinal fluid amyloid β-protein is conversely reduced, and thus measuring this is helpful in the diagnosis of Alzheimer's disease.

Non-Patent Document 1: Lisa R. Fodero, Javier Saez-Valero, Maria-Sagrario Barquero, Alberto Marcos, Catriona A. McLean and David H. Small; "Wheat germ agglutinin-binding glycoproteins are decreased in Alzheimer's disease cerebrospinal fluid", Journal of Neurochemistry, 2001, 79, 1022-1026; and Non-Patent Document 2: Susan J. van Rensburg, Peter Berman, Felix Potocnik, Pam MacGregor, Dinie Hon and Nico de Villiers; "5- and 6-glycosylation of transferrin in patients with Alzheimer's disease", Metabolic Brain Disease, 2004, Vol. 19, 89-96.

DISCLOSURE OF THE INVENTION

Mean(s) to Solving the Problem(s)

With regard to the diagnosis of Alzheimer's disease using tau proteins, since dementias increasing phosphorylated tau protein along with neurofibrillary tangles are not limited to Alzheimer's disease, it is difficult to distinguish from other types of dementia (tauopathies). Moreover, one problem is that neuronal apoptosis is already progressing during the period in which phosphorylated tau protein is elevated, and thus even if treatment is started during this period, full recovery is not expected.

Furthermore, while the amyloid β-protein employing this diagnostic marker is correlated with the severity of late-stage Alzheimer's disease, there is virtually nothing out of the ordinary during the premorbid stages (mild cognitive impairment: MCI) or early stages thereof. Moreover, a decrease in amyloid β-protein is not specific to Alzheimer's disease. In addition, individuals vary significantly, and even interpreting that there is uniform decrease thereof in Alzheimer's disease is difficult.

An ideal marker should be capable of diagnosis before apoptosis of neurocytes, and preferably capable of diagnosis of preclinical Alzheimer's disease. Moreover, it should also be capable of differential diagnosis between a normal brain and other types of dementia and easily screening a large number of individuals. However, as mentioned above, the markers that have been proposed so far have all been far from ideal, and thus insufficient at performing a reliable diagnosis. Accordingly, at the present time, no conclusive marker for the diagnosis of Alzheimer's disease has been found.

Moreover, although WGA binding protein is anticipated as being a new marker for the diagnosis of Alzheimer's disease, the details thereof are unclear (Non-Patent Document 1). Moreover, since it was reported that the increase was only seen in a specific polymorphic transferrin having a sugar chain with six sialic acids attached thereto, and no significant changes were seen with regard to other types of sugar chains (Non-Patent Document 2), the possibility of employing transferrin sugar chains (other than that having six sialic acids) in the diagnosis of Alzheimer's disease was thought to be low.

In view of such problems, an objective of the present invention is the development of a novel diagnostic kit, diagnostic marker, and detection method that is highly effective in the diagnosis Alzheimer's disease.

Mean(s) to Solving the Problem(s)

According to the present invention, a diagnostic kit for diagnosing Alzheimer's disease is provided, which includes a detection means for quantitatively detecting transferrin having a sugar chain with a varying number of sialic acids attached thereto, and shows the quantitative ratio between transferrin having a sugar chain with one or two sialic acids attached thereto and transferrin having a sugar chain with three or four sialic acids attached thereto in a cerebrospinal sample obtained from a mammal, as an indicator of the pathological state of Alzheimer's disease. This diagnostic kit indicates a specific sugar chain of transferrin showing a specific quantitative change in Alzheimer's disease, and thus is advantageous in the diagnosis of early stage Alzheimer's disease, and the differential diagnosis between Alzheimer's disease and other types of dementia that are manifested by similar symptoms.

Moreover, according to the present invention a diagnostic kit for diagnosing Alzheimer's disease is provided, which includes a detection means for quantitatively detecting transferrin having a sugar chain with a varying number of sialic acids attached thereto, and shows an either an amount of variation in transferrin having a sugar chain with one or two sialic acids attached thereto, or an amount of variation in transferrin having a sugar chain with three or four sialic acids attached thereto, in a cerebrospinal sample obtained from a mammal, with respect to cerebrospinal fluid obtained from a normal mammal of the same species, as an indicator of the pathological state of Alzheimer's disease. This diagnostic kit indicates a specific sugar chain of transferrin showing a specific quantitative change in Alzheimer's disease, and thus is advantageous in the diagnosis of early stage Alzheimer's disease, and the differential diagnosis between Alzheimer's disease and other types of dementia that are manifested by similar symptoms.

Furthermore, according to the present invention, a diagnostic kit for diagnosing Alzheimer's disease is provided, which includes a detection means quantitatively detecting transferrin, and a detection means for quantitatively detecting transferrin having a sugar chain attached thereto, and shows an indicator obtained by totaling the amount transferrin and the amount of transferrin having a sugar chain attached thereto, in a blood sample obtained from a mammal, as an indicator of the pathological state of Alzheimer's disease. This diagnostic kit uses the amount of transferrin having a sugar chain attached thereto showing a specific quantitative change in Alzheimer's disease as an indicator, and thus is advantageous in the diagnosis of early stage Alzheimer's disease, and the differential diagnosis between Alzheimer's disease and other types of dementia that are manifested by similar symptoms.

Moreover, according to the present invention, a diagnostic kit for diagnosing Alzheimer's disease is provided, which includes a detection means quantitatively detecting transferrin, a detection means for quantitatively detecting transferrin having a sugar chain attached thereto, and a detection means for quantitatively detecting transferrin having a sugar chain with a varying number of sialic acids attached thereto, and shows an indicator obtained by totaling the amount of transferrin in a blood sample obtained from a mammal, the amount of transferrin having a sugar chain attached thereto in that blood sample, and the amount of transferrin having a sugar chain with one or two sialic acids attached thereto and/or transferrin having a sugar chain with three or four sialic acids attached thereto, in a cerebrospinal sample obtained from that mammal, as an indicator of the pathological state of Alzheimer's disease. This diagnostic kit shows the total amount of transferrin having a sugar chain attached thereto in blood and transferrin specific sugar chains showing a specific quantitative change in Alzheimer's disease, and thus is advantageous in the diagnosis of early stage Alzheimer's disease, and the differential diagnosis between Alzheimer's disease and other types of dementia that are manifested by similar symptoms.

Furthermore, according to the present invention, a diagnostic kit for diagnosing Alzheimer's disease is provided, which includes lectin for quantitatively detecting transferrin having a sugar chain with a varying number of sialic acids attached thereto by a lectin enzyme-linked immunosorbent assay. This kit quantitatively detects transferrin sugar chains that are showing a specific quantitative change in Alzheimer's disease by a simple lectin enzyme-linked immunosorbent assay and, which is a modified ELISA, and thus it allows for a large volume of samples to be easily, cheaply, or reliably digitized and processed.

Moreover, according to the present invention, a diagnostic marker for diagnosing Alzheimer's disease is provided, which includes a quantitative ratio of transferrin having a sugar chain with one or two sialic acids attached thereto, and transferrin having a sugar chain with three or four sialic acids attached thereto. This diagnostic marker indicates a transferrin specific sugar chain showing a specific quantitative change in Alzheimer's disease, and thus may be employed as a diagnostic marker allowing the diagnosis of early stage Alzheimer's disease, and the differential diagnosis between Alzheimer's disease and other types of dementia that are manifested by similar symptoms.

Furthermore, according to the present invention, a diagnostic marker for diagnosing Alzheimer's disease is provided, which includes transferrin having a sugar chain with one or two sialic acids attached thereto, or transferrin having a sugar chain with three or four sialic acids attached thereto. This diagnostic marker shows a transferrin specific sugar chain showing a specific quantitative change in Alzheimer's disease, and thus may be employed as a diagnostic marker allowing the diagnosis of early stage Alzheimer's disease, and the differential diagnosis between Alzheimer's disease and other types of dementia that are manifested by similar symptoms.

Moreover, according to the present invention, a diagnostic marker for diagnosing Alzheimer's disease is provided, which includes an indicator obtained by totaling the amount of transferrin, and the amount transferrin having a sugar chain attached thereto, in a blood sample. This diagnostic marker indicates a transferrin specific sugar chain showing a specific quantitative change in Alzheimer's disease, and thus may be employed as a diagnostic marker allowing the diagnosis of early stage Alzheimer's disease, and the differential diagnosis between Alzheimer's disease and other types of dementia that are manifested by similar symptoms.

Furthermore, according to the present invention, detection method for an indicator of the pathological state of Alzheimer's disease is provided, which includes a step of quantitatively detecting transferrin having a sugar chain with a varying number of sialic acids attached thereto, and a step of calculating the quantitative ratio of transferrin having a sugar chain with one or two sialic acids attached thereto, to transferrin having a sugar chain with three or four sialic acids attached thereto, for a cerebrospinal fluid sample obtained from a mammal. This detection method allows for the detection of a pathological indicator enabling diagnosis of early stage Alzheimer's disease, and the differential diagnosis between Alzheimer's disease, by the measurement of a transferrin specific sugar chain showing a specific change in Alzheimer's disease as a measuring subject thereof.

Furthermore, according to the present invention, detection method for an indicator of the pathological state of Alzheimer's disease is provided, which includes a step of quantitatively detecting transferrin having a sugar chain with a varying number of sialic acids attached thereto, for a cerebrospinal sample obtained from a mammal; and a step of calculating an amount of variation in transferrin having a sugar chain with one or two sialic acids attached, or an amount of variation in transferrin having a sugar chain with three or four sialic acids attached thereto, with respect to normal tissue obtained from the same species of mammal. This detection method allows for the detection of a pathological indicator enabling diagnosis of early stage Alzheimer's disease, and the differential diagnosis between Alzheimer's disease, by the measurement of a transferrin specific sugar chain showing a specific change in Alzheimer's disease as a measuring subject thereof.

Moreover, according to the present invention, detection method for an indicator of the pathological state of Alzheimer's disease is provided, which includes a step of quantitatively detecting transferrin, a step of quantitatively detecting transferrin having a sugar chain attached thereto, and a step of calculating an indicator totaling the amount of transferrin and the amount of transferrin having a sugar chain attached thereto, for a blood sample obtained from a mammal. This detection method allows for the detection of a pathological indicator enabling diagnosis of early stage Alzheimer's disease, and the differential diagnosis between Alzheimer's disease, by the measurement of a transferrin specific sugar chain showing a specific change in Alzheimer's disease as a measuring subject thereof.

Moreover, the abovementioned, diagnostic kit, diagnostic marker, and detection method, are merely one embodiment of the present invention, and thus a according to the present invention, a method employing these for the diagnosis of Alzheimer's disease is also provided.

Effects of the Invention

The present invention allows for a diagnosis that is highly correlated with the pathology of Alzheimer's disease to be performed.

BRIEF DESCRIPTION OF THE DRAWINGS

FIG. 1 shows the structure of a transferrin sugar chain.

PREFERRED MODE FOR CARRYING OUT THE INVENTION

Figure 2:
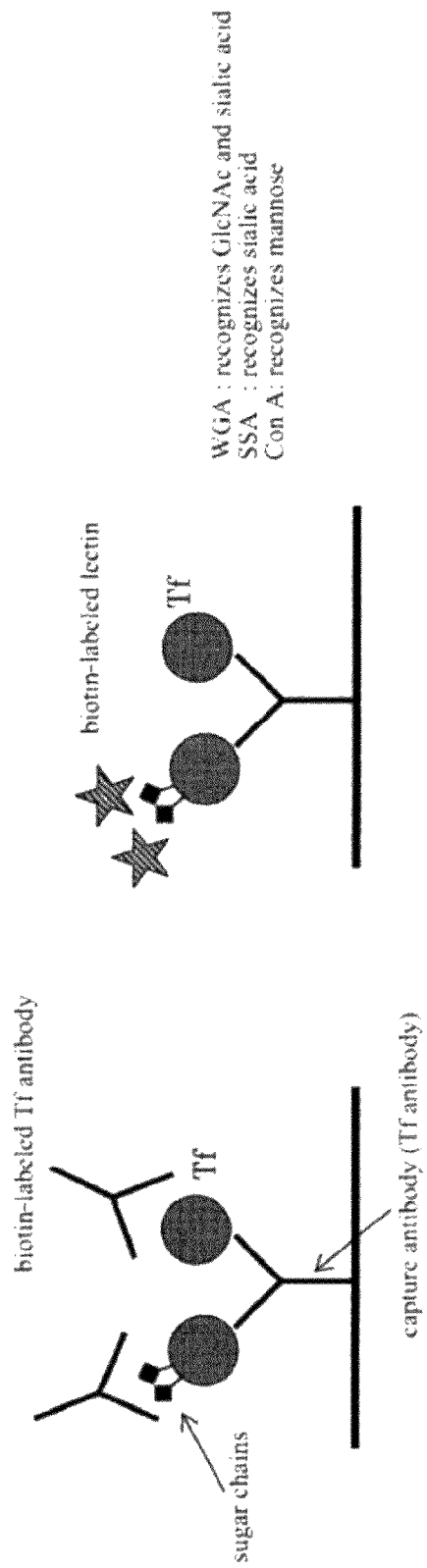
FIG. 2 is a schematic view of a lectin enzyme-linked immunosorbent assay.

The "Alzheimer's disease" (AD) of the present embodiment is seen as atrophy of the cerebral cortex, and pathologically, in addition to a high degree of neuronal loss, is referred to as dementia when characteristic lesions such as neurofibrillary tangles or senile plagues are observed, and senile dementia of Alzheimer's type when dementia arises from Alzheimer's disease. Among these pathological changes, senile plague is thought to be the earliest manifested, and the most significant change in Alzheimer's disease of the characteristic changes thereof. The major component of senile plague is amyloid β-protein (Aβ), and since there are mutations in the beta-amyloid precursor protein (βAPP), which is an Aβ precursor gene in familial Alzheimer's disease showing autosomal dominant inheritance, the abnormal degradation or production of Aβ is thought to be strongly related to the pathogenesis and progress of Alzheimer's disease. Aβ is generated by being sequentially cleaved from amyloid precursor protein by β-secretase and γ-secretase (presenilin complex), a type of aspartic protease. Diagnosis of Alzheimer's disease (senile dementia of Alzheimer's type) is clinically performed based on whether various diagnostic standards have been satisfied, based on an evaluation of functional neuroimaging, physiological tests, neuropsychological tests, and clinical symptoms.

The "an indicator of the pathological state of Alzheimer's disease" of the present embodiment refers to an indicator relating the pathology of Alzheimer's disease, which includes for example, the onset of Alzheimer's disease, senile dementia of Alzheimer's type, and the like. Thus, the pathological indicator for Alzheimer's disease includes for example, an indicator for the prediction of the degree of risk for onset of senile dementia of Alzheimer's type, the prediction and/or diagnosis of early stage Alzheimer's disease, the estimation of the degree of brain dysfunction, clinical comprehension, the prediction of the course of the disease, the observation and/or evaluation of therapeutic results, prognosis prediction, and the like. The above-mentioned conditions, and the parameters indicating such a condition, may be easily monitored by common techniques that are well known to doctors in this technical field.

The "mammal" of the present embodiment refers to an arbitrary mammal, including a human being, a domestic animal, a pet, a zoo animal, or a sports animal. For example, it may include a dog, a cat, a cow, a pig, a horse, a rabbit, and the like. Preferably the mammal is a human.

The "transferrin (Tf)" of the present embodiment refers to a protein that is substantially identical to a glycoprotein having 679 amino acids generally referred to as transferrin, and which also includes a genetic polymorph, a genetic variant, or a splicing variant thereof. Transferrin is a plasma protein produced mainly in the liver that works as an iron transport molecule by binding two atoms of iron per molecule thereof, and is known to be involved in in vivo hematopoietic function and iron metabolism. With regard to the relationship between transferrin and Alzheimer's disease, although various studies have been conducted as result of the relationship between polymorphisms of transferrin genes, whether or not a relationship exists between a genetic polymorph and Alzheimer's disease remains inconclusive.

The "sugar chain" of the present embodiment is a polysaccharide having at least one sugar glycosidically-linked to a protein, which consists primarily of sugars such as N-acetyl-D-glucosamine, N-actyl-D-galactosamine, D-mannose, D-galactose, L-fucose, and sialic acid. The sugar chains are primarily divided into two major types: O-linked oligosaccharides and N-linked oligosaccharides, with each of the characteristic saccharide compositions thereof being known. The role of sugar chains in intermolecular adhesion and/or interaction (linkage) is very well known, as they play an important part in cell adhesion, the immune system, the nervous system, and the like.

With regard to transferrin sugar chains, N-linked oligosaccharides having N-acetylglucosamine, mannose, galactose, and sialic acid each attached to asparagine 413 and asparagine 611, respectively, are known (see FIG. 1). Transferrin is classified into several isoforms, depending on the number of sialic acids attached in the final step of glycosylation, and normal serum transferrin is tetrasialotransferrin with four sialic acids. Transferrins having one sialic acid, two sialic acids, three sialic acids, and four sialic acids all exist in the cerebrospinal fluid. With regard to the analysis of transferrin sugar chains in Alzheimer's disease, several reports thereof are known. For example, there are reports citing that an increase in transferrins having a sugar chain with six sialic acids attached thereto was found, and still others citing that significant changes were not seen with regard to an increase and decrease in transferrins having a sugar chain with five sialic acids attached thereto (Non-Patent Document 2). However, none of these reports suggest or consider the efficacy thereof as diagnostic marker resulting from differential experimentation of tauopathies and the like, and thus they also lack a practical application.

The "lectin" of the present embodiment refers to a protein that recognizes specific sugar chains and forms bonds or cross-links to a glycoprotein or glycolipid, including a variant and modifier thereof. Moreover, the "lectin" of the present embodiment in includes a wide variety of proteins that bind specifically to sugar chains as a receptor for a sugar chain or a receptor for molecule having a sugar chain, and as such, the scope thereof is not strictly limited to lectin. Lectin is preferably a protein binding to a glycoprotein. Depending on the lectin, the structural characteristics of the sugar chain binding thereto may differ, and thus lectins that are complementary to a glycolipid, a glycoprotein, and various sugar chains are known. In addition to mammalian-derived lectins, insect-derived and plant-derived lectins are well known. For example, WGA (wheat germ agglutinin), SSA (*Sambucus sieboldiana* agglutinin; a sialic acid-specific Japanese elderberry bark lectin that specifically recognizes α-2,6-sialylated sialic acid), LCA (*Lens culinaris* agglutinin; a mannose-specific lectin), and the like are known.

The "antibody" of the present invention is a protein, generally referred to as an "antibody", which recognizes various molecules such as low molecular weight compounds, specific polysaccharides, or specific peptides and forms cross-links or bonds thereto, and which also includes variants and modifiers thereof. Various types of antibodies are known, such as rabbit-derived, mouse-derived, and sheep-derived antibodies. Moreover, specific monoclonal antibodies may be produced by cultivating cells, or may also be produced in eukaryotic cells or coliform bacteria using a genetic engineering technique, and thus also includes recombinants thereof. Furthermore, the fragments of the abovementioned types of antibodies are also included within the present scope. As an antibody fragment, an F(ab')2 fragment, an Fab' fragment and the like, may be exemplified. Additionally, in a case where the antibody is a monoclonal antibody, the globulin type is not specifically limited in any way. For example, IgG, IgM, IgA, IgE, IgD, and the like, may be provided. Moreover, the monoclonal antibody may also be a humanized antibody.

Furthermore, in each embodiment of the present invention, a labeled lectin or a labeled antibody that is linked to the antibody or lectin itself and a labeling substance that is capable of generating a signal in order to detect or measure an antibody or lectin may also be employed. In such a case, in addition to being linked directly thereto, the antibody or lectin and labeling compound may also be linked by the employment of an avidin-biotin system, a streptavidin-biotin system, or a secondary antibody, which are included within the scope of present invention. As a secondary antibody in such a case, an antibody capable of attaching to a lectin or a primary antibody may be used.

In a case where an enzyme is employed as a label, horseradish peroxidase, alkaline peroxidase, glucose oxidase, β-galactosidase, glucoamylase, carbonate dehydratase, acetylcholine esterase, lysozyme, malonate dehydrogenase, glucose-6-phosphate dehydrogenase, for example, may be employed. As a method labeling with these enzymes, a method of oxidizing a sugar chain of the enzyme with periodic acid and linking an amino acid of a lectin or antibody to an aldehyde group generated thereby, or a method of introducing a group, such as a maleimide group or pyridyl sulfide group, into the enzyme and linking a thiol group present in the Fab' fragment of a lectin or antibody, may be exemplified.

In a case where an enzyme is employed as a label, since the free labeled antibody or lectin is removed by washing after the test sample and labeled antibody or lectin has been incubated, the labeled antibody or lectin can be detected by measuring a chromogenic reaction and the like via the action of the substrate of the abovementioned labeled enzyme. For example, in a case where being labeled by peroxidase, a brown or yellow color is produced by the combining of O-phenylenediamine or diaminobenzidine as the coloring reagent and hydrogen peroxide as the substrate. In a case where being labeled by glucose oxidase, 2,2'-azino-bis(3-ethyl-benzthiazoline-6-sulfonic acid) (ABTS), and the like, may be employed as the substrate.

In a case where employing fluorescent dye as the label, the antibody or lectin may be labeled by a fluorescent dye, such as fluorescein isothiocyanate (FITC) or tetramethylrhodamine B isothiocyanate (TRIT). The binding of the fluorescent dye and lectin or antibody may also be performed by a conventional method.

In a case where employing a color labeling substance as the label, a colored latex or colloidal metal, and the like, may be employed as the label. As a representative example of the colloidal metal, metal colloid particulate may be provided as dispersed particles of gold sol, silver sol, selenium sol, tellurium sol, or platinum sol, and the like. Ordinarily, the size of the metal colloid particulate is preferably approximately 3 nm to 60 nm in diameter. Moreover, as a representative example of the colored latex, synthetic latex, such as polystyrene latex colored by a red coloring agent, a blue coloring agent, and the like, may be provided. As the latex, natural latex such as natural rubber latex may be employed. The size of the colored latex may be selected from a diameter of approximately several thousand nm to several hundred nm. These color labeling substances may use a commercial product employed as is. However, they may also be processed, or manufactured by a known method therefor.

The binding of the color labeling substance and the antibody or lectin may be performed by a conventional known method. For example, in a case where the color labeling substance is a metal colloid particulate provided as the dispersed particles of gold sol, the physical linking of the antibody and gold sol may be conventionally performed via the mixing both of these at room temperature.

Moreover, in addition thereto, a radioisotope label and the like (e.g., $^{125}I$, $^{131}I$, $^{3}H$, $^{14}C$, and the like), may also be employed as the label, and thus is included within the scope of the present invention.

The "enzyme-linked immunosorbent assay (ELISA)" refers to a method for quantitatively detecting antigens for antibodies by using an enzyme-labeled antibody, which is superior in quantitative capability, convenience, and certainty (reproducibility), and thus widely employed in clinical tests, and the like. Enzyme-linked immunosorbent assays are very well known technology, and thus a known paper or document can be referred to for the details of a common technical means. As the enzyme-linked immunosorbent assay, several methods are known. Among these a sandwich ELISA method refers to a very widely known method, in which an antigen is linked to a capture antibody fixed to a plate, and then a detection antibody detects the capture antibody-linked antigen.

The "lectin enzyme-linked immunosorbent assay (lectin ELISA)" refers to a modified enzyme-linked immunosorbent assay using lectin rather than the antibody of a enzyme-linked immunosorbent assay to detect a substance having a sugar chain, and thus it is capable of quantitatively detecting a substance having sugar chain such as a glycoprotein, by using an enzyme-labeled lectin (FIG. 2). Similarly to enzyme-linked immunosorbent assays, lectin enzyme-linked immunosorbent assays are superior in their quantitative capability (numerical capability), convenience, and certainty (reproducibility). Because enzyme-linked immunosorbent assays are such well-known technology, and lectin enzyme-linked immunosorbent assays are a modified method thereof, a known enzyme-linked immunosorbent assay related paper or document can be referred to for the details of a general technical means thereof.

With regard to the lectin enzyme-linked immunosorbent assay, a sandwich lectin ELISA, which is a modified method of a sandwich ELISA, may also be employed. In such cases, a combination of two lectins may be employed, or combination of an antibody and lectin may be employed. In a case where lectin is used in combination with an antibody, depending on the antibody employed, a lectin-reactive sugar chain may be present, and therefore the lectin of the present embodiment is employed after enzyme processing or the like, is conducted.

The abovementioned enzyme-linked immunosorbent assay (ELISA) and lectin enzyme-linked immunosorbent assay (lectin ELISA) is not specifically limited to a lectin ELISA or ELISA employing an enzyme as the label, and thus may also include a modified method, such as a fluoroimmunoassay employing a fluorescent substance as the label, or radioimmunoassay (RIA) employing a radioisotope as the label. When applying each of these immunochemical measuring, no particular condition or operational setup is required, and thus a known paper or document can be referred to for the details thereon.

EMBODIMENTS

Hereinafter, the embodiments of the present invention will be explained.

In an embodiment of the present invention, a diagnostic kit for diagnosing Alzheimer's disease includes a detection means for quantitatively detecting transferrin having a sugar chain with a varying number of sialic acids attached thereto, and shows a quantitative ratio between transferrin having a sugar chain with one or two sialic acids attached thereto and transferrin having a sugar chain with three or four sialic acids attached thereto, in a cerebrospinal sample obtained from a mammal, as an indicator of the pathological state of Alzheimer's disease, to thereby allow for the pathology of Alzheimer's disease to be understood. For example, with regard to this kit, in a case where a decrease in the ratio of transferrin having a sugar chain with one or two sialic acids attached thereto to transferrin having a sugar chain with three or four sialic acids attached thereto is observed, with respect to normal tissue obtained from a mammal of the same species, the possibility of Alzheimer's disease is diagnosed as being high. However, this kit is not specifically limited thereto, and as such, other Alzheimer's disease related symptoms/conditions may also be monitored by common techniques that are well known to doctors in this technical field, and the pathological indicator according to the present embodiment may allow for the easy diagnosis thereof.

Moreover, in another embodiment of the present invention, the diagnostic kit for diagnosing Alzheimer's disease includes a detection means for quantitatively detecting transferrin having a sugar chain with a varying number of sialic acids attached thereto, in a cerebrospinal sample obtained from a mammal, and shows either an amount of variation in transferrin having a sugar chain with one or two sialic acids attached thereto, or an amount of transferrin having a sugar chain with three or four sialic acids attached thereto, in a cerebrospinal sample obtained from a mammal, with respect to a cerebrospinal fluid obtained from a normal mammal of the same species, as an indicator of the pathological state of for Alzheimer's disease, to thereby allow for the pathology of Alzheimer's disease to be understood.

Preferably, the amount of variation indicated by the abovementioned diagnostic kit, may also be a decrease in transferrin having a sugar chain with one or two sialic acids attached thereto, or an increase in transferrin having a sugar chain with three or four sialic acids attached thereto, with respect to normal tissue obtained from a mammal of the same species. For example, in the present kit, in a case where a decrease in transferrin having a sugar chain with one or two sialic acids attached thereto, or an increase in transferrin having a sugar chain with three or four sialic acids attached thereto is observed, with respect to cerebrospinal obtained from a mammal of the same species, the possibility of Alzheimer's disease is diagnosed as being high. However, this kit is not specifically limited thereto. Other Alzheimer's disease related symptoms/conditions may also be monitored by common techniques that are well known to doctors in this technical field, and thus a pathological indicator for these may be also easily obtained by using the diagnostic kit according to the present embodiment.

Moreover, in another embodiment of the present invention, the diagnostic kit for diagnosing Alzheimer's disease includes a detection means for quantitatively detecting transferrin, and a detection means for quantitatively detecting transferrin having a sugar chain attached thereto, and shows an indicator obtained by totaling the amount of transferrin, and the amount of transferrin having a sugar chain attached thereto, in a blood sample obtained from a mammal, as an indicator of the pathological state of Alzheimer's disease, to thereby allow for the pathology of Alzheimer's disease to be understood.

The indicator employed by this kit is obtained by conducting a conventionally employed statistical process using the amount of transferrin with a sugar chain attached thereto in blood showing a significant change in Alzheimer's disease and the amount of transferrin in blood showing similar changes in Alzheimer's disease, to preferably clarify a difference therebetween. Although this kind of indicator can be calculated via a conventional procedure that is well known to researchers and doctors in the field of clinical diagnosis, and although it employs a quantitative ratio between transferrin and transferrin having a sugar chain attached thereto (possibility of being diagnosed with Alzheimer's disease is high when this ratio is high), it should be understood that so long as it is an effective indicator using the actual measured values of both the amount transferrin having a sugar chain attached thereto and the amount of transferrin, it is not specifically limited thereto.

Conventionally, although the differential diagnosis between other dementias such as a tauopathy has been difficult, even in a case where a biological diagnostic marker was employed, the abovementioned diagnostic kit allows for a diagnosis that is highly specific to Alzheimer's disease, and for a more effective treatment method to be provided. Moreover, since it differs from conventional diagnostic kits in that it allows for a diagnosis to be made based on a change that is even observed in early stage Alzheimer's disease, it is particularly advantageous in the diagnosis of early stage or premorbid stage Alzheimer's disease, and thus makes effective prophylaxis or treatment possible.

Furthermore, the abovementioned kit employing cerebrospinal fluid allows for noninvasive testing, and for a large number of samples to be rapidly and easily processed. Moreover, since cerebrospinal fluid surrounds the brain, it is possible to obtain diagnostic results that are even more highly correlated with a pathological condition of the brain. The cerebrospinal fluid is not limited specifically to intraventricular cerebrospinal fluid, and thus lumbosacral cerebrospinal fluid may also be used. In a case where lumbosacral cerebrospinal fluid is used, diagnosis may be performed with even less risk to a living subject. With regard to the collection of cerebrospinal fluid, the cerebrospinal fluid collection may use a conventionally employed means, such as cisternal tap, lumbar tap, ventricular tap, or spinal tap and the like, depending on the circumstances.

Moreover, the abovementioned kit employing blood allows for diagnosis be performed even easier and faster, and with greater convenience for the patient. In such a case, it is also possible to obtain blood serum in which the presence of lymphocytes is reduced to a negligible level by performing an appropriate centrifuge operation on the blood and to react a detection reagent therewith, and thus is included in the present embodiment.

In addition, it is also possible for the diagnosis via the abovementioned diagnostic kit using a blood sample to be performed as a primary screening, which is even easier, faster, and more convenient for the patient, and for diagnosis via the abovementioned diagnostic kit using a cerebrospinal sample to be performed as a secondary diagnosis; and thus both are included in the present embodiment. In such a case, a pathological indicator that also totals the amount of transferrin and an amount of transferrin having a sugar chain attached thereto in blood employed for the primary screening may also be employed at the time of secondary diagnosis.

Here, a sample obtained from cerebrospinal fluid, blood, blood serum, and the like, may optionally undergo a single processing step or a plurality of processing steps. Although, a process of saturating the transferrin with iron ions, a process of purifying the target substance and removing impurities by a immunoprecipitation method or various columns, a process of fragmenting proteins by trypsin and the like, a process of removing a specific sugar chain via an enzyme or another enzymatic process, various chemical modifications thereto, and the like may be exemplified as the processing step(s) thereof, the processing step(s) thereof are not specifically limited thereto.

Furthermore, in all of the embodiments of the present invention, the description of "protein" refers to something that also includes a peptide fragment, or in some cases, a sugar chain fragment and the like, after a process, such as the abovementioned chemical process, enzymatic process, or fragmentation process has been conducted on a protein in a sample, and thus even in a case where the object to be detected via these sample pre-processing steps or the like is changed into something other than a protein, it is understood as being included within the technical scope of the present invention.

Moreover, in another embodiment of the present invention, the diagnostic kit for diagnosing Alzheimer's disease includes a detection means quantitatively detecting transferrin, a detection means for quantitatively detecting transferrin having a sugar chain attached thereto, and a detection means for detecting transferrin having a sugar chain with a varying number of sialic acids attached thereto, and shows an indicator obtained by totaling the amount of transferrin in a blood sample obtained from a mammal, the amount of transferrin having a sugar chain attached thereto in that blood sample, and the amount of transferrin having a sugar chain with one or two sialic acids attached thereto and/or transferrin having a sugar chain with three or four sialic acids attached thereto, in a cerebrospinal sample obtained from that mammal, as an indicator of the pathological state of Alzheimer's disease, to thereby allow for the pathology of Alzheimer's disease to be understood.

This kit allows for diagnosis to be performed with an even higher degree of accuracy, by employing an indicator combining the amount of transferrin in blood, the amount of transferrin having a sugar chain attached thereto in a blood sample, the amount of transferrin having a sugar chain with one or two sialic acids attached thereto and/or the amount of transferrin having a sugar chain with three or four sialic acids attached thereto in a cerebrospinal, which show changes in Alzheimer's disease. This indicator is obtained via a statistical process using the amount of transferrin in a blood sample, the amount of transferrin with a sugar chain attached thereto in a blood sample, the amount of transferrin having a sugar chain with one or two sialic acids attached thereto and/or the amount of transferrin having a sugar chain with three or four sialic acids attached thereto in a cerebrospinal fluid sample, to preferably clarify a difference therebetween. This kind of indicator can be calculated via a common technique that is well known to researchers and doctors in the field of clinical diagnosis.

Furthermore, in still another embodiment of the present invention, the above-mentioned diagnostic kit is one in which the transferrin sugar chain is a WGA or SSA binding sugar chain, to thereby allow for the pathology of Alzheimer's disease to be more accurately understood. Since a transferrin having a WGA or SSA binding sugar chain is observed as an even more definite quantitative change in Alzheimer's disease, the use of these allows for an even more reliable diagnosis to be performed.

Furthermore, in still another embodiment of the present invention, the abovementioned kit detects transferrin having a sugar chain attached thereto by performing lectin affinity electrophoresis using a gel containing lectin as a detection means therefor. In electrophoresis with a gel containing lectin, since the mobility of a protein having a sugar chain that binds to a target lectin from an applied point is low when the lectin binding affinity (binding strength) thereof is high, it is possible for a transferrin with only a few sugar chains (weak lectin binding strength) and a transferrin with a high sugar chain binding affinity to be clearly separated. Preferably, the lectin is a lectin recognizing a sugar chain having sialic acid. In the present embodiment, for example, western blot analysis may be further performed with a transferrin antibody after lectin affinity electrophoresis of the sample; or staining may be further conducted by a protein staining reagent, such as Coomassie brilliant blue, or western blot analysis, or lectin blot analysis, after lectin affinity electrophoresis of the sample, and thus so long as one is skilled in the art, various condition adjustments and design modifications may be easily applied, based on known techniques in the art.

The lectin affinity electrophoresis, for example, may be performed by a procedure such as that mentioned below. A lectin-containing agarose gel is prepared, and the sample is electrophoresed. The sample of cerebrospinal, blood or blood serum is electrophoresed, and then the protein is electrically transferred from the gel to a PVDF membrane. Next, the protein that was transferred to the membrane is probed with anti-transferrin antibody as the primary antibody and anti-IgG antibody as the secondary antibody. The secondary antibody uses an IgG alkaline phosphatase label or peroxidase label, as well as a chromogenic substrate thereof, to produce a visible color. Or, a cerebrospinal fluid, or blood that was pre-purified by immunoprecipitation via the anti-transferrin antibody may be used as the sample. In such cases, post-electrophoresis detection is performed by staining the protein in the gel with a protein staining method, such as Coomasie brilliant blue stain, or silver stain, in order to make it visible. Moreover, the protein is electrically transferred to the PVDF membrane, made visible by performing a protein staining method on the transferred membrane, and probed. Although it is thought that a protein stain is also contaminated with other proteins at the time of immunoprecipitation, a method of further probing the membrane by anti-transferrin antibody may also be exemplified as one method for increasing detection accuracy. The above-mentioned procedure is an example of a specific procedure, and thus the present embodiment is not limited specifically thereto.

Moreover, in still another embodiment of the present invention, the abovementioned kit detects glycosylated transferrin by performing western blot analysis using sugar chain recognizing antibody or lectin blot analysis using lectin as the detection means thereof. Blotting with an antibody or lectin that binds specifically to a sugar chain allows for transferrin to be identified. Preferably, the lectin is one that recognizes a sugar chain with sialic acid. In addition, the recognition of transferrin having different sugar chain conformations can be further ensured via a combination of isoelectric focusing, immunoprecipitation, chromatography, and the like. During detection, for example, an antibody or lectin labeled by various enzymes, or an enzyme-labeled secondary antibody may be employed, and thus so long as one is skilled in the art, various conditional adjustments and design modifications may be easily applied, based on known techniques in the art.

As the sugar chain recognizing antibody, for example, a known sugar chain recognizing antibody, such as that described in Sato et al., Trends in Glycoscience and Glycotechnology, 2004 September, Vol. 16, No. 91, or Sato et al., Trends in Glycoscience and Glycotechnology, 1999 November, Vol. 11, No. 62, pp. 371-390 may be employed; or a sugar chain recognizing antibody may be prepared. In a case where the sugar chain recognizing antibody is prepared, it can be prepared with reference to a preparation method described in a cited reference relating to antibodies of the abovementioned reference documents, or prepared by the below-mentioned method.

In a case where a sugar chain recognizing polyclonal antibody is prepared, for example, the preparation thereof may be by immunizing a warm-blooded animal with a complex of a carrier protein or another carrier molecule and a sugar chain or a portion thereof, or transferrin having a sugar chain attached thereto or a portion of peptide, or a combination thereof, collecting blood containing the polyclonal antibody from that immunized animal, and isolating and purifying the antibody.

An example of a preparation method will be indicated hereinafter. So long as the mixing ratio of the antigen, the carrier, and various carrier proteins allows the antibody for the antigen immunized by cross-linking the carrier to be efficiently mixed, the conditions thereof are arbitrary. For example, a method may be employed whereby bovine serum albumin, bovine thyroglobulin, hemocyanin, or the like, is coupled to antigen at a weight ratio of approximately 0.1 to 20 per antigen, preferably at ratio of approximately 1 to 5. Moreover, various condensing agents may be employed in the coupling of the carrier and antigen. For example, an active ester reagent containing glutaraldehyde or carboiimide, maleimide active ester, thiol group, dithiopyridyl group, and the like, may be employed. In a case where a small molecule is employed as the antigen, the utilization of a carrier protein is particularly preferable.

The antigen or antigen-carrier complex itself is administered at to an antibody producing site of a warm-blooded animal, or administered along with the appropriate diluent, buffer solution, and carrier. In order to increase the antibody production capability at the time of administration, for example, a conventionally employed adjuvant, such as Freund's complete adjuvant, Freund's incomplete adjuvant, RAS [MPL (Monophosphoryl Lipid A)+TDM (Synthetic Trehalose Dicorynomycolate)+CWS (Cell Wall Skeleton) adjuvant system], aluminum hydroxide, and the like, may be administered. The antigen and these adjuvants may be administered in the form of an emulsified liquid or a suspension liquid employing a diluent. Here, the adjuvant refers to a substance that when administered along with an antigen nonspecifically intensifies the immunological response to that antigen.

As the immunized warm-blooded animal, for example, a mammal such as a rabbit, mouse, hamster, a guinea pig, a chicken, a rat, a dog, a goat, a sheep, a cow, and the like, may be employed. For example, as the method of immunization, a method of immunization that is conventionally known to one who is skilled in the art may be used, such as immunization by administering the antigen more than once. Specifically, the antigen administration may be performed once, usually every one to six weeks, for a total of two to ten doses. With regard to the dosage amount for a single dose, for example, approximately 0.05 mg to 2 mg of the antigen can be used as a guideline. The route of administration is also not particularly limited in any way, and thus may be arbitrarily selected from subcutaneous administration, intradermal administration, intraperitoneal administration, intravenous administration, intramuscular administration, for example. However, administration via an intravenous injection, intraperitoneal injection, or subcutaneous injection is preferable. After the immunized mammal is housed for one-half month to 4 months, a small sample of blood serum is collected from the auricular vein or the like, of said mammal, so that the antibody titers can be measured. When the antibody titer is elevated, the administration of the antibody is executed at a suitable frequency, in accordance with the circumstances thereof. For example, a booster may be administered using 10 μg to 1000 μg of the antigen. Measurement of the antibody titer, for example, may be conducted by measuring the activity of the labeling agent coupled to the antibody from the antiserum and labeled protein that are reacted.

Using a conventional method, blood or peritoneal fluid is collected from a mammal one to two months after being immunized with its final dose, the complement system is passivated by processing at 56 degrees Celsius for 30 minutes, and a polyclonal antibody is obtained by affinity chromatography, without separation and purification. As the affinity carrier, for example, an antigen peptide immobilized in a gel, such as Affigel, may be employed. Or, the obtained blood may be separated and purified, for example, by a conventional method, such as ion exchange chromatography, gel filtration chromatography, ammonium sulfate or polyethylene glycol precipitation, centrifugation, and the like.

In a case where a sugar chain recognizing monoclonal antibody was prepared, the preparation thereof, for example, may be by immunizing a warm-blooded animal with a complex of a carrier protein or another carrier molecule and a sugar chain or a portion thereof, or transferrin having a sugar chain attached thereto, or a portion of peptide, or a combination thereof, collecting splenocytes, B lymphocytes, lymph node cells, or the like, from that immunized animal, obtaining a monoclonal antibody producing hybridoma via cell fusion between a myeloma cell line and the obtained cells, and isolating monoclonal antibodies from that hybridoma.

An example of a preparation method will be indicated hereinafter. Up to the step of the immunization of a warm-blooded mammal, the preparation may be conducted via a preparation method similar to that of the abovementioned preparation method employed for a polyclonal antibody. As the warm-blooded animal to be immunized, a monkey, a rabbit, a dog, a guinea pig, a mouse, a rat, a sheep, a goat, or a chicken may be exemplified. However, it is preferable that a mouse or rat is employed. For example, as the method of immunization, a method of immunization that is conventionally known to one who is skilled in the art may be used, such as immunization by administering the antigen more than once. Specifically, the antigen administration may be performed once, usually about every one to six weeks, for a total of approximately two to ten doses. For example, approximately 0.05 mg to 2 mg of the antigen can be used as a guideline therefor. The route of administration is also not particularly limited in any way, and thus may be arbitrarily selected from subcutaneous administration, intradermal administration, intraperitoneal administration, intravenous administration, intramuscular administration, for example. However, administration via an intravenous injection, intraperitoneal injection, or subcutaneous injection is preferable.

An individual with an antibody titer was selected from the warm-blooded animals immunized with the antigen, the lymph node or spleen was collected about two to five days after the final immunization, and the antibody producing cells, such as the splenocytes, lymph node cells, or lymphocytes contained therein were obtained. The measurement of the antibody titer of the antiserum thereof, for example, may be conducted by measuring the activity of the labeling agent coupled to the antibody from the antiserum and labeled protein that are reacted.

Subsequently, the fusion of the myeloma (myeloma cells) and antibody producing cells thereof may be conducted by a known fusion method, for example, it may follow that of Kohler and Milstein (G. Kohler et al., Nature, 1975, vol. 256, p. 495 (1975)). As the fusion promoting agent, for example, polyethylene glycol (PEG), or Sendai virus may be exemplified. However, it is preferable that PEG is employed. As the myeloma, NS-1, P3U1, SP2/0, AP-1, and the like, may be exemplified. However, in particular, P3U1, SP2/0, or P363XAg8 are preferable in mice. The preferred ratio between the number of myelomas and the number of antibody producing cells employed is approximately 1:1 to 20:1, and an even more efficient cell fusion can be achieved by adding PEG (preferably, PEG 1000 to PEG6000) at a concentration of approximately 10% to 80%, and cultivating the cells 20 degrees Celsius to 40 degrees Celsius, preferably at 30 degrees Celsius to 37 degrees Celsius, for 1 to 10 minutes.

Hybridoma selective cultivation and screening can be performed by a conventional mammalian cell culture technique, in which HAT (hypoxanthine, aminopterin, thymidine) is added thereto. Moreover, any culture may be used as a breeding culture, so long as it is capable of growing a hybridoma. For example, an RPMI-1640 culture supplemented with 1% to 20% bovine fetal serum, preferably with 10% to 20% fetal bovine serum; a GIT culture (manufactured by Wako Pure Chemical Industries, Ltd.) supplemented with 1% to 10% bovine fetal serum; or a protein-free hybridoma culture (SFM-101, manufactured by Nissui Pharmaceutical Co., Ltd.), or the like, may be employed. The culture temperature thereof is normally 20 degrees Celsius to 40 degrees Celsius, and preferably approximately 37 degrees Celsius. The culture time is normally five days to three weeks, and preferably one week to two weeks. The cultivation thereof is normally performed under 5% carbon dioxide gas. Moreover, the hybridoma obtained by cell fusion may be cloned may by a limiting dilution method, and the like.

The screening of each hybridoma producing monoclonal antibody may employ various methods. For example, a method in which a hybridoma culture supernatant is added to a solid phase (e.g., microplate) having an antigen absorbed directly thereto or along with a carrier, protein G, protein A, or an anti-immunoglobulin antibody (antibody reacting with the same type of immunoglobulin as that of the cell producing antibody employed in cell fusion) labeled primarily with a radioactive substance, an enzyme, or the like is then added, and the monoclonal antibody linked to the solid phase is detected; a method in which a hybridoma culture supernatant is added to a solid phase having an anti-immunoglobulin absorbed, protein A, or protein G absorbed thereto, an antigen labeled by a radioactive substance, an enzyme, or the like is then added, and a monoclonal antibody linked to the solid phase is detected; and the like, may be employed.

With regard to the production of the intended monoclonal antibody from the hybridoma selected in this manner, the hybridoma may be cultured by a peritoneal fluid formation method or a conventional cell cultivation method, and the monoclonal antibody may be purified from peritoneal fluid or the culture supernatant. The purification of the monoclonal antibody from the peritoneal fluid or culture supernatant can be performed by a conventional method. For example, it can be performed according to a method of immunoglobulin separation and purification [e.g., salting-out method, alcohol precipitation method, isoelectric point precipitation method, electrophoresis method, absorption and desorption method using an ion-exchanger (e.g., DEAE), ultracentrifugation method, gel filtration method, affinity chromatography, specific purification method in which only the antibody is recovered using an antigen-binding phase or active absorbent such as protein A or Protein G, and its binding is dissociated to yield the antibody].

Moreover, an IgM antibody is frequently obtained as the monoclonal antibody for the sugar chain, and in such cases the IgM may be used as is, or the IgM may be modified by a genetic engineering method that is well known to those skilled in the art and then used.

The above are examples, and thus so long as one is skilled in the art, in order to obtain the intended sugar chain recognizing antibody, various condition adjustments and design modifications may be easily applied, based on a known antibody production method.

Furthermore, in still another embodiment of the present invention, the abovementioned kit is one which detects transferrin having a sugar chain attached thereto by performing enzyme-linked immunosorbent assay using a sugar chain recognizing antibody or lectin enzyme-linked immunosorbent assay using lectin as the detection means thereof. The diagnostic kit according to the present embodiment is technology that is already been established, and by employing a lectin enzyme-linked immunosorbent assay which is a modified method for an enzyme-linked immunosorbent assay in which lectin is used, or employing an enzyme-linked immunosorbent assay that frequently used even in actual clinical practice, it allows for a digitized measurement to be performed simply, reliably and economically, and for the processing of a large number of samples. Preferably, the lectin recognizes a sugar chain with sialic acid.

The enzyme-linked immunosorbent assay or lectin enzyme-linked immunosorbent assay according to the present embodiment may be performed by the below-mentioned procedure (see FIG. 2), for example. To begin with, an anti-transferrin antibody is immobilized on an ELISA microplate. Next, the sample solution (e.g., cerebrospinal fluid or blood) is added after being blocked by bovine serum albumin, and the antibody is then linked to the transferrin in the sample (primary reaction). After the unbound antibody is rinsed, the biotin labeled lectin (e.g., SSA or WGA) or the sugar chain recognizing antibody is reacted (secondary reaction). Then, HRP (horseradish peroxidase) recognizing streptavidin is linked thereto, it is colored by TMB (3,3',5,5'-tetramethylbenzidine) reagent, a reaction stopping solution (e.g. sulfuric acid) is added, and then it is measured at absorbance of 450 nm. When preparing calibration curve with a standard reference sample containing the intended sugar at a known concentration beforehand, the quantitative values can be calculated based on the absorbance obtained above.

Moreover, in the enzyme-linked immunosorbent assay or the lectin enzyme immunoassay via the abovementioned sandwich method, a mixture of at least two of the abovementioned lectins or antibodies may be employed with the objective of improving the sensitivity of the measurement and the like, without requiring only one type of the lectin or sugar chain recognizing antibody to be employed in the labeled antibody or immobilized antibody. In the measurement method of the present embodiment via a sandwich method, the lectin or antibody employed in a primary and secondary reaction is preferably one that employs different binding sites for the antigen or sugar chain.

The above procedure is provided only as an example, and thus so long as one is skilled in the art, various modifications can be made, based on the procedures of a conventional enzyme-linked immunosorbent assay. As such a modification, for example, blocking with a known blocking agent (including commercial products, such as BlockAce, or the like, which is manufactured by Dianippon Sumitomo Pharma Co., Ltd., or by GE Healthcare Bio-Sciences, Ltd.) other than BSA, immobilizing the antibody or lectin on a microplate, and performing detection by an antibody separate antibody; or immobilizing the sample directly on the microplate, and performing detection by an antibody or lectin; or by using a secondary antibody for the antibody, or lectin or antibody linked directly to HRP at the time of detection, without an avidin-biotin system; or using another known enzyme or substrate instead of HRP or TMB, and using coloring, luminescence, fluorescence and the like, in the detection thereof; may be exemplified, and as such, are also included within the present embodiment.

Moreover, in still another embodiment of the present invention, the abovementioned kit detects transferrin having a sugar chain attached thereto by performing an antibody array using an antibody array chip with sugar chain recognizing antibody mounted thereon, or a lectin array using a lectin array chip with lectin mounted thereon as the detection means. By employing a lectin array or antibody array, it allows simple analysis, or for multifaceted simultaneous analysis of other proteins and like, which contain multiple factors. Particularly, by combining an antibody recognizing other factors and a lectin or a sugar chain recognizing antibody, it is possible to measure additional confirmations of a sugar chain with multiple factors at one time, and to provide a more detailed analysis of the etiology and pathological state of the disease. Preferably, the lectin is one that recognizes a sugar chain having sialic acid. The lectin chip according to the present embodiment provides a method including the steps for fixing the lectin to the chip, by applying a manufacturing method for an antibody array.

As the antibody or lectin employed in the array chip, an antibody or lectin (e.g., SSA or WGA) recognizing a sugar chain of transferrin is used, at least one arbitrary probe (not specifically limited to an antibody or lectin) is included per one spot of the microarray chip, and the antibody or lectin recognizing a sugar chain of at least one type of transferrin is included at various spots. The lectin or antibody and probe may also be fixed to the microarray chip by being chemically bound or physically bound thereto, and in such cases, an operation raising the sensitivity of a porous or fixed substrate to the base may be further added thereto.

The raw material of the microarray may be of any known material, and is preferably a material employed by a conventional microarray. Moreover, a tertiary structural component or cellulose nitrate or a reactive base capable of allowing the antibody or lectin or other probe to be fixed to the surface of the chip may also be included. For example, a porous material and a polymeric film such as silicon wafer, glass, film, polycarbonate, polystyrene, polyurethane may be exemplified. The fixation of the lectin or antibody, or another probe may employ a conventional microarray production method. For example, the formation of spots may be performed by a method such as, a photolithography method, piezoelectric printing method, micropipetting, or spotting.

Although the spots on the array chip, for example, may have a diameter 50 μm to 500 μm, and a spotting interval of 10 μm to 500 μm, it is preferable that the density and size of the spots are suitably adjusted by the resolution of the array analyzing system. The array according the present embodiment is equipped with a microwell plate, for example, a 96-well well plate, and employs an automatic device (e.g., Biomek, or Genetix robo) utilizing an existing 96-well plate, to allow for the mechanical processing of a sample molecule, label, hybridization, and washing.

With regard to the measurement and implementation of the array, it may be operated in a substantially similar manner to a conventional antibody array. For example, the transferrin is pre-labeled with a fluorescent substance such as Cy3 or Cy5 or the like, and amount of binding is detected as the amount of label fluorescence by a special detector. The amount of label fluorescence thereof (amount of binding to the lectin) is quantified by analytic software, and the sugar chain structure of transferrin is analyzed and measured. The amount of lectin and sugar chain binding is based on the strength/weakness of an affinity therefor, with weaker affinities being more difficult to detect. Thus, as a detection method of a fluorescent probe labeled with a protein, a method may be tried which allows for a highly sensitive labeling substance or binding amount to be detected, for example, by evanescent wave excitation that is capable of detecting a probe attached to a substrate with a high degree of sensitivity. The above are merely examples, and thus, in addition to directly labeling the transferrin, so long as one is skilled in the art, various condition adjustments and design modifications, such as labeling the transferrin with a labeled antibody and the like, may also be applied, based on known procedures.

Furthermore, in still another embodiment of the present invention, the above-mentioned diagnostic kit detects transferrin with a sugar chain attached thereto using WGA or SSA as the lectin. Employing WGA or SSA as the lectin allows for the reliable detection of the conformations of the sugar chains of transferrin to be possible.

Moreover, in still another embodiment of the present invention, the above-mentioned diagnostic kit detects transferrin with a sugar chain attached thereto using an antibody recognizing a sugar chain with sialic acid. Employing the antibody recognizing a sugar chain with sialic acid allows for a more detailed detection of the conformations of the sugar chains, and for a detailed diagnosis of a pathological condition.

As the antibody recognizing a sugar chain with sialic acid, for example, a known sugar chain recognizing antibody, such as that described in Sato et al., Trends in Glycoscience and Glycotechnology, 2004 September, Vol. 16, No. 91, or Sato et al., Trends in Glycoscience and Glycotechnology, 1999 November, Vol. 11, No. 62, pp. 371-390 may be employed; or a sugar chain recognizing antibody may be prepared.

In a case where the antibody recognizing a sugar chain with sialic acid is prepared, it can be prepared by a method substantially similar to the abovementioned production method for a sugar chain recognizing antibody. In such cases, employing an antigen having a sugar chain including sialic acid as the antigen allows for the intended antibody to be obtained.

Furthermore, in still another embodiment of the present invention, the above-mentioned diagnostic kit detects transferrin with a sugar chain attached thereto using an antibody recognizing transferrin having a sugar chain attached thereto. Employing the antibody recognizing transferrin having a sugar chain attached thereto allows for the specific and easy detection of a conformation of a sugar chain of transferrin, without it being combined with lectin or another antibody.

In a case where the antibody recognizing transferrin having a sugar chain attached thereto is prepared, it can be prepared by a method substantially similar to the abovementioned production method for a sugar chain recognizing antibody. In such cases, by employing transferrin having a sugar chain attached thereto, which has been obtained, for example, by purification from cells, an enzymatic modification, or chemical modifier and the like, the intended antibody can be obtained. Or, for example, asparagine residue 413 and asparagine residue 611 of transferrin and a sugar chain that is attached to a peptide adjacent to an essentially identical amino acid may also be employed as the antigen. Moreover, an IgM antibody is frequently obtained as the monoclonal antibody against the sugar chain, and in such cases the IgM may be used as is, or the IgM may also be modified by a genetic engineering method that is well known to those skilled in the art and then used. Furthermore, the sugar chain in these cases is preferably a sugar chain having sialic acid, and which may be obtained by employing a sugar chain having sialic acid as the antigen.

Moreover, in still another embodiment of the present invention, a diagnostic kit is for diagnosing Alzheimer's disease, and includes lectin for quantitatively detecting transferrin having a sugar chain with a varying number of sialic acids attached thereto by a lectin enzyme-linked immunosorbent assay, and as such, it allows for the diagnosis of early stage Alzheimer's disease, and the differential diagnosis between Alzheimer's disease and other types of dementia that are manifested by similar symptoms to be easily performed. In addition, it also allows for a large volume of samples to be easily processed or for digitized measurements.

Furthermore, in still another embodiment of the present invention, the above-mentioned diagnostic kit quantitatively detects transferrin with a sugar chain attached thereto by a lectin enzyme-linked immunosorbent assay using WGA or SSA as the lectin. The lectin enzyme-linked immunosorbent assay using WGA or SSA as the lectin allows for the reliable detection of a conformation of a sugar chain of transferrin.

Moreover, aside from the abovementioned embodiment, various in vivo assays or mass spectrometry may also be utilized as the detection means for a glycosylation state of transferrin. Mass spectrometry is widely known as a method of analysis for the gylcosylation state of a protein, and thus, so long as one is skilled in the art, various condition adjustments and design modifications may also be applied, based on known procedures. For example, the gylcosylation state of transferrin can be easily accomplished, and as such, is included within the technological scope of the present invention. Detection using mass spectrometry allows for the easy detection thereof. In addition, in comparison with another method using a test reagent, it is also advantageous from the standpoint of the automation thereof.

Furthermore, as an in vivo assay, exposing a body fluid from the body of the patient (e.g., cerebrospinal fluid, or blood) to an antibody or lectin labeled by a detectable labeling substance such as a radioisotope, and evaluating the binding of the antibody or lectin to the body fluid or cells thereof by biopsy or external radioactive scanning, may also be exemplified, and thus should obviously be included within the technical scope of the present invention. A real-time analysis of a living patient allows for diagnosis and a more detailed elucidation of the pathological state of the patient to be performed.

Moreover, in still another embodiment of the present invention, a diagnostic marker for diagnosing Alzheimer's disease includes a ratio between transferrin having a sugar chain with one or two sialic acids attached thereto and transferrin having a sugar chain with three or four sialic acids. The use of this diagnostic marker allows for a pathological state of Alzheimer's disease to be understood. For example, with regard to this diagnostic marker, in a case where a decrease in the ratio of transferrin having a sugar chain with one or two sialic acids attached thereto to transferrin having a sugar chain with three or four sialic acids attached thereto is observed, with respect to normal tissue obtained from a mammal of the same species, the possibility of Alzheimer's disease is diagnosed as being high. However, this marker is not specifically limited thereto, and as such, other Alzheimer's disease related symptoms/conditions may also be monitored by common techniques that are well known to doctors in this technical field, and the disease marker according to the present embodiment may allow for the easy diagnosis thereof.

Furthermore, in still another embodiment of the present invention, a diagnostic marker for diagnosing Alzheimer's disease includes transferrin having a sugar chain with one or two sialic acids attached thereto or transferrin having a sugar chain with three or four sialic acids. The use of this diagnostic marker allows for a pathological state of Alzheimer's disease to be understood. Preferably, with regard to this diagnostic kit, an amount of variation in transferrin having a sugar chain with one or two sialic acids attached thereto or an amount of variation in transferrin having a sugar chain with three or four sialic acids attached thereto, with respect to normal tissue obtained from a mammal of the same species, may be an indicator of the pathological state of Alzheimer's disease. Preferably, the variation may also be a decrease in transferrin having a sugar chain with one or two sialic acids attached thereto, or an increase in transferrin having a sugar chain with three or four sialic acids attached thereto, with respect to normal tissue obtained from a mammal of the same species.

For example, with regard to this diagnostic marker, in a case where a decrease in transferrin having a sugar chain with one or two sialic acids attached thereto, or an increase in transferrin having a sugar chain with three or four sialic acids attached thereto is observed, with respect to normal tissue obtained from a mammal of the same species, the possibility of Alzheimer's disease is diagnosed as being high. However, this marker is not specifically limited thereto, and as such, other Alzheimer's disease related symptoms/conditions may also be monitored by common techniques that are well known to doctors in this technical field, and the diagnostic marker according to the present embodiment may allow for the easy diagnosis thereof.

Moreover, in another embodiment of the present invention, a diagnostic marker for diagnosing Alzheimer's disease includes an indicator obtained by totaling an amount of transferrin and an amount of transferrin having a sugar chain attached thereto, in a blood sample obtained from a mammal, to thereby allow for a pathological state of Alzheimer's disease to be understood. The indicator employed by this diagnostic kit is obtained by conducting a conventionally employed statistical process, using the amount of transferrin with a sugar chain attached thereto in blood showing a significant change in Alzheimer's disease and the amount of transferrin in blood showing similar changes in Alzheimer's disease, to preferably clarify a difference therebetween. This type of indicator can be calculated via a conventional procedure that is well known to researchers and doctors in the field of clinical diagnosis, and thus a quantitative ratio between transferrin having a sugar chain attached thereto and transferrin (possibility of being diagnosed with Alzheimer's disease is high when this ratio is high), and the like, may be exemplified. It should also be understood that, so long as it is an effective indicator using the actual measured values of both the amount transferrin having a sugar chain attached thereto and the amount of transferrin, it is not specifically limited thereto.

Furthermore, it should be understood that the employment of a diagnostic marker including an indicator obtained by combining these diagnostic markers, and using the amount of transferrin in a blood sample, the amount of transferrin with a sugar chain attached thereto in a blood sample, and the amount of transferrin having a sugar chain with one or two sialic acids attached thereto and/or the amount of transferrin having a sugar chain with three or four sialic acids attached thereto in a cerebrospinal fluid sample, to perform a statistical process preferably that preferably clarifies a difference therebetween This kind of indicator can be calculated via a common technique that is well known to researchers and doctors in the field of clinical diagnosis.

Conventionally, although the differential diagnosis between other dementias such as a tauopathy has been difficult, even in a case where a biological diagnostic marker was employed, the abovementioned diagnostic kit allows for a diagnosis that is highly specific to Alzheimer's disease, and for a more effective treatment method to be provided. Moreover, since it differs from conventional diagnostic markers, and is a marker derived from changes that are even observed in early stage Alzheimer's disease, it allows for the planning of an effective therapeutic treatment before the progression of symptoms.

Furthermore, in another embodiment of the present invention, a detection method for an indicator of the pathological state of Alzheimer's disease includes a step of quantitatively detecting transferrin having a sugar chain with a varying number of sialic acids attached thereto, and a step of calculating the quantitative ratio of transferrin having a sugar chain with one or two sialic acids attached thereto to transferrin having a sugar chain with three or four sialic acids attached thereto, for a cerebrospinal fluid sample obtained from a mammal. The detection method according to the present embodiment detects changes in the number of sialic acids of a sugar chain of a specific transferrin, and calculates a quantitative ratio thereof, to allow for diagnosis of early stage Alzheimer's disease or the differential diagnosis between other types of dementia.

Moreover, in another embodiment of the present invention, a detection method for an indicator of the pathological state of Alzheimer's disease includes a step of quantitatively detecting transferrin having a sugar chain with a varying number of sialic acids attached thereto in a cerebrospinal fluid sample obtained from a mammal; and a step of calculating an amount of variation in transferrin having a sugar chain with one or two sialic acids attached thereto, or an amount of variation in transferrin having a sugar chain with three or four sialic acids attached thereto, with respect to a cerebrospinal fluid sample obtained from a normal mammal of the same species. The detection method according to the present embodiment detects changes in the number of sialic acids of a sugar chain of a specific transferrin, and from there among also detects the amount of sugar chains having one or two, or three or four acids sialic attached thereto, to allow for diagnosis of early stage Alzheimer's disease or the differential diagnosis between other types of dementia.

Furthermore, in another embodiment of the present invention, a detection method for an indicator of the pathological state of Alzheimer's disease includes a step of quantitatively detecting transferrin, a step of quantitatively detecting transferrin having a sugar chain attached thereto, and a step of calculating an indicator totaling an amount of transferrin, and an amount of transferrin having a sugar chain attached thereto, for a blood sample obtained from a mammal. The detection method according to the present embodiment primarily detects the amount of a specific transferrin having a sugar chain attached thereto in the blood of one with Alzheimer's disease, to allow for diagnosis of early stage Alzheimer's disease or the differential diagnosis between other types of dementia. The indicator calculated by this detection method is obtained by conducting a conventionally employed statistical process, using the amount of transferrin with a sugar chain attached thereto in blood showing a significant change in Alzheimer's disease and the amount of transferrin in blood showing similar changes in Alzheimer's disease, to preferably clarify a difference therebetween. This kind of indicator can be calculated via a conventional procedure that is well known to researchers and doctors in the field of clinical diagnosis, and thus a quantitative ratio between transferrin having a sugar chain attached thereto and transferrin (possibility of being diagnosed with Alzheimer's disease is high when this ratio is high), and the like, may be exemplified. It should also be understood that, so long as it is an effective indicator using the actual measured values of both the amount transferrin having a sugar chain attached thereto and the amount of transferrin, it is not specifically limited thereto.

Moreover, a diagnostic kit described by the abovementioned embodiment is a diagnostic marker or detection method that is disclosed with the intention of exemplifying the present invention, and as such is not specifically limited thereto. The technical scope of the present invention is defined by the description of the claims, and thus, so long as one is skilled in art, various design modifications may be applied to the technical scope of invention described in the claims. For example, the detection of a transferrin having a sugar chain attached thereto may also be achieved by various immunochemical techniques, a slot or dot blot assay, or various modified electrophoretic methods, such as two-dimensional electrophoresis, and the like, and thus, it is obvious that the diagnostic kit, diagnostic marker, and detection method of these embodiments are included in the technical scope of the present invention.

As the various immunochemical techniques mentioned above, a method of competitively reacting a labeled antigen and an antigen in a sample solution with an antibody, separating the non-reacted labeled antigen (F) and a labeled antigen (B) bonded to the antibody (B/F separation), measuring the labeled amount of either B or F, and quantifying the amount of antigen in the sample fluid (Competitive method), may be exemplified. As the method of B/F separation, a liquid phase method of using a soluble antibody as the antibody, and performing B/F separation by using a secondary antibody against a high molecular phase (e.g., polyethylene glycol) and the soluble antibody; and a solid phase method of using an immobilized antibody as the primary antibody or a soluble primary antibody and an immobilized secondary antibody, may be exemplified. Moreover, as another immunochemical technique, a method of separating a solid phase and liquid phase after competitively reacting a solid phase antigen and an antigen in a sample solution with a given amount of a labeled antibody; or reacting an excess amount of a labeled antibody and antigen in a sample solution, then adding an immobilized antigen to bond a non-reacted labeled antibody to the solid phase, separating the solid phase and liquid phase, measuring the labeled amount of either phase, and quantifying the amount of antigen in the sample solution (Immunometric method), may be exemplified. Furthermore, a method of measuring the amount of insoluble precipitate resulting from an antigen-antibody reaction in a solution or gel (Nephelometry method), may be exemplified. Even in a case where the amount of antigen in the sample solution is negligible and only a small amount of precipitate is obtained, laser nephelometry utilizing laser scattering and the like, may be employed.

Moreover, glycosylated transferrin may also be detected by performing chromatofocusing a chromatofocusing column as the detection means, for example. Chromatofocusing is a chromatographic technique for forming a pH gradient in a column to separate proteins based on their isoelectric points. Thus, performing chromatofocusing capable of separating substances based on their charge allows for a transferrin having different sugar chains to be clearly separated based number of negatively charged sialic acids present in a sugar chain. In addition, a post-chromatofocusing treatment sample may easily undergo further treatments, so that a plurality of continuous treatments can be easily performed. As the specific procedure for chromatofocusing, a known procedure, or one referred to in technical literature from a column manufacturer/distributor, such as GE Healthcare Bio-Sciences, Ltd., or Beckman Coulter, Inc., and the like, may easily be implemented, as well as the application of various condition adjustments and design modifications thereto.

Specifically, for example, a sample is added to a column balanced with a high pH buffer, and then the substances in the sample are eluted in descending order of isoelectric points by switching stepwise to low pH eluents to form a pH gradient in a column. For example, using a special column including a carrier into which various types of anionic exchange groups are introduced as the column, and using an amphoteric buffer containing a uniform buffer capacity covering a wide pH range as the eluent. As the special column, Mono P Columns of GE Healthcare Bio-Sciences, Ltd., and the like, are known. However, so long as one is skilled in the art, a column may be arbitrarily selected and employed based on a target substance or conditions, and the like. Since chromatofocusing is such well-known technology, even with regard to the procedures and the like thereof, a known paper or document can be referred to for the details of a general technical means thereof. In addition thereto, a technical document relating to a chromatofocusing column such as the abovementioned Mono P Columns, and the like, may also be referred to.

In the present embodiment, for example, a sample may be subjected to chromatofocusing, then further subjected to conventional electrophoresis, and finally subjected to western blot analysis with a transferrin antibody; or a sample that is first immunoprecipitated with a transferrin antibody may be subjected to chromatofocusing, then further subjected to conventional electrophoresis, and finally subjected to lectin blot analysis, western blot analysis, or staining by a protein staining reagent, such as Coomassie brilliant blue, and the like; or a sample may be subjected to chromatofocusing, then further subjected to analysis by a lectin array/antibody array, or a lectin enzyme-linked immunosorbent assay/enzyme-linked immunosorbent assay. Thus, so long as one is skilled in the art, various condition adjustments and design modifications may be easily applied, based on known techniques in the art.

Furthermore, for example, the transferrin having a sugar chain attached thereto may be detected by performing isoelectric focusing isoelectric focusing gel as the detection means. Performing chromatofocusing, which is capable of separating substances based on charge, allows for transferrin having different sugar chains to be clearly separated based on the number of negatively charged sialic acids present in a sugar chain present a sugar chain. In present embodiment, for example, a sample may be subjected to isoelectric focusing, and then further subjected to western blot analysis with a transferrin antibody; or a sample that is first immunoprecipitated with a transferrin antibody may be subjected to isoelectric focusing, and further subjected to lectin blot analysis, or staining by a protein staining reagent, such as Coomassie brilliant blue, and the like. Thus, so long as one is skilled in the art, various condition adjustments and design modifications may be easily applied, based on known techniques in the art.

Moreover, an embodiment according to the present invention is a manufactured item including the diagnostic kit according to the present invention. The manufactured item may include a container and a label or package insert mounted on a container. The container, for example, includes a bottle, a vial, a syringe, and the like, selected from a suitable raw material, such as glass or plastic, and the like. The container stores a composition including a diagnostic kit according to the present invention, and depending on the circumstances, the configuration thereof may also be provided with a sterile access port (e.g., an intravenous solution vial having a stopper that is pierceable by a hypodermic needle). The label or package insert indicates a composition employed for the diagnosis of hepatitis. The label or package insert further includes a written warning when used in diagnosis. The manufactured item may be further provided with an additional container including a control sample, each buffer solution, a diluent, a filter, a needle, a syringe, and bacteriostatic water (BWFI) for injection.

In accordance with an embodiment in which a diagnostic kit includes the above-mentioned manufactured item, the antibody or lectin may be pre-immobilized, or pre-labeled. The phase that can be employed in the diagnostic kit according to an embodiment of the present invention is not specifically limited in any way. For example, an insoluble carrier, a polymer such as polystyrene, glass beads, magnetic particles, a microplate, filter paper for immunochromatography, a glass filter, and the like, may be provided. The manufactured item mentioned above may further include another optional component. As another optional component, an labeling enzyme, a substrate thereof, a radioisotope, a luminescent substance, a fluorescent material, a coloring material, a buffer solution, a plate, and the like, may be exemplified. However, the present embodiment is not specifically limited thereto.

Moreover, the abovementioned diagnostic kit, diagnostic marker, and detection method are merely one embodiment of the present invention, and as such, according to the present invention, a method for the diagnosis of Alzheimer's disease using these may also be provided, as well as allow for a diagnosis that is highly correlated with the pathology of Alzheimer's disease to be performed via this diagnostic method.

As such a diagnostic method, for example, a method for diagnosis of Alzheimer's disease may be provided, which includes a step of quantitatively detecting transferrin having a sugar chain with a varying number of sialic acids attached thereto for a blood sample obtained from a mammal, and a step of calculating the quantitative ratio of transferrin having a sugar chain with one or two sialic acids attached thereto, with respect to transferrin having a sugar chain with three or four sialic acids attached thereto, in that cerebrospinal fluid sample.

Furthermore, a method for diagnosis Alzheimer's disease may also be provided, which includes a step of quantitatively detecting transferrin having a sugar chain with a varying number of sialic acids attached thereto, for a cerebrospinal fluid sample obtained from a mammal, and a step of calculating an amount of variation in transferrin having a sugar chain with one or two sialic acids attached thereto, or an amount of variation in transferrin having a sugar chain with three or four sialic acids attached thereto, with respect to a normal tissue sample obtained from a mammal of the same species.

Moreover, a method for diagnosis Alzheimer's disease may also be provided, which includes a step of quantitatively detecting transferrin; a step of quantitatively detecting transferrin having a sugar chain attached thereto; and a step of calculating an indicator which totals the amount of transferrin, and the amount of transferrin having a sugar chain attached thereto, for a blood sample obtained from a mammal.

Furthermore, a method for diagnosing Alzheimer's disease may also be provided, which includes a detection means for quantitatively detecting transferrin, a detection means for quantitatively detecting transferrin having a sugar chain attached thereto, for a blood sample obtained from a mammal, a detection means for quantitatively detecting transferrin having a sugar chain with a varying number of sialic acids attached thereto, for a cerebrospinal fluid sample obtained from a mammal, and step of calculating an indicator which totals the amount of transferrin, the amount of transferrin having a sugar chain attached thereto in that blood sample, and the amount of transferrin having a sugar chain with one or two sialic acids attached thereto and/or transferrin having a sugar chain with three or four sialic acids attached thereto, in that cerebrospinal sample.

Moreover, the abovementioned diagnostic method may also provide that the above-mentioned indicator is a ratio between transferrin and transferrin having a sugar chain attached thereto.

Furthermore, the abovementioned diagnostic method may also provide that the abovementioned sugar chain is a WGA or SSA binding sugar chain.

Moreover, the abovementioned diagnostic method may also provide that the transferrin having a sugar chain attached thereto and/or the transferrin having sugar chain with a varying number of sialic acids is quantitatively detected by lectin affinity electrophoresis using lectin.

Furthermore, the abovementioned diagnostic method may also provide that the transferrin having a sugar chain attached thereto and/or the transferrin having sugar chain with a varying number of sialic acids is quantitatively detected by lectin blot analysis using lectin or western blot analysis using a sugar chain recognizing antibody.

Moreover, the abovementioned diagnostic method may also provide that the transferrin having a sugar chain attached thereto and/or the transferrin having sugar chain with a varying number of sialic acids is quantitatively detected by a lectin enzyme-linked immunosorbent assay using lectin or an enzyme-linked immunosorbent assay using a sugar chain recognizing antibody.

Furthermore, the abovementioned diagnostic method may also provide that the transferrin having a sugar chain attached thereto and/or the transferrin having sugar chain with a varying number of sialic acids is quantitatively detected by use of a lectin array or an antibody array.

Moreover, the abovementioned diagnostic method may also provide that the above-mentioned sugar chain recognizing antibody is a sialic acid recognizing antibody.

Furthermore, the abovementioned diagnostic method may also provide that the abovementioned sugar chain recognizing antibody is an antibody recognizing transferrin having a sugar chain attached thereto.

Moreover, a method for diagnosing Alzheimer's disease may also be provided, which includes a step of quantitatively detecting the transferrin having a sugar chain with a varying number of sialic acids attached thereto, for a cerebrospinal fluid sample obtained from a mammal, by a lectin enzyme-linked immunosorbent assay.

Furthermore, the abovementioned diagnostic method may also provide that the abovementioned lectin is WGA or SSA.

In addition, the employment of the diagnostic kit, diagnostic marker, detection method and diagnostic method, and the like, described in the abovementioned embodiments, a method of screening a malignant substance or therapeutic agent for Alzheimer's disease, a method of analyzing a pathological state, in a human being or mammal, are also included in the technical scope of the present invention.

EXAMPLES

Hereinafter, the present invention will be explained in greater detail with reference to the Examples. However, it should be noted that these are only Examples, and as such, the present invention should not be considered as being specifically limited thereto. Moreover, unless specifically indicated, a commercial reagent referred to by the Examples, is to be used in accordance with the directions of a manufacturer thereof.

Example 1

Detection of WGA Reactive Glycoproteins in Cerebrospinal Fluid

From a period of December 2003 to March 2006, studies on 50 Alzheimer's disease (AD) cases, 43 non-dementia (non-AD) cases, and 14 tauopathy (dementias other than AD) cases, were allowed at Tottori University. Six normal cases from the 43 non-dementia cases were also employed in some of the Examples. Moreover, the 14 tauopathy cases included: five cases of progressive supranuclear palsy, four cases of dementia with Lewy Bodies, and five cases of corticobasal degeneration. The organization of these subjects is indicated in Table 1.

TABLE 1

Organization of Patient Population

| | Number of patients (male/female) | Average age + standard deviation (average male/female age + SD) |
|---|---|---|
| Alzheimer's disease | 50 (19/31) | 73 ± 8 (74 ± 8/72 ± 8) |
| Tauopathy | 14 (10/4) | 72 ± 7 (73 ± 3/68 ± 14) |
| (Details) | | |
| Progressive supranuclear palsy | 5 (3/2) | 67 ± 9 |
| Dementia with Lewy Bodies | 4 (3/1) | 76 ± 5 |
| Corticobasal degeneration | 5 (5/0) | 71 ± 7 |
| Non-dementia comparison group | 38 (21/17) | 71 ± 10 (71 ± 8/72 ± 12) |
| (Including normal cases) | 6 (1/5) | 64 ± 14 |

The diagnosis of each patient was performed by taking a detailed medical history, performing a physical examination, performing a neurological examination, performing a higher brain function test, performing an imaging test (CT, MRI, SPECT), and the like, with reference to the below-mentioned criteria. The diagnostic criteria being satisfied were, the DSM-IV and NINCDS-ADRA diagnostic criteria for Alzheimer's disease, the NINDS-SPSP diagnostic criteria for progressive supranuclear palsy, the Dementia with Lewy Bodies Consensus Guidelines for dementia with Lewy Bodies, and the Rinne, Morimatsu et al. criteria for corticobasal degeneration.

When these studies were conducted, an informed consent form was obtained from the patient or the research protocol (research proposal) followed the WORLD MEDICAL ASSOCIATION DECLARATION OF HELSINKI Ethical Principles for Medical Research Involving Human Subjects of 1975, and they were performed under the approval of the Tottori University Ethics Committee.

In present the Example, cerebrospinal fluid was collected from the subjects via a conventional method, and the WGA binding glycoprotein existing in the cerebrospinal fluid was separated by electrophoresis and detected. Hereinafter, the procedure therefor will be explained in greater detail.

Figure 3:
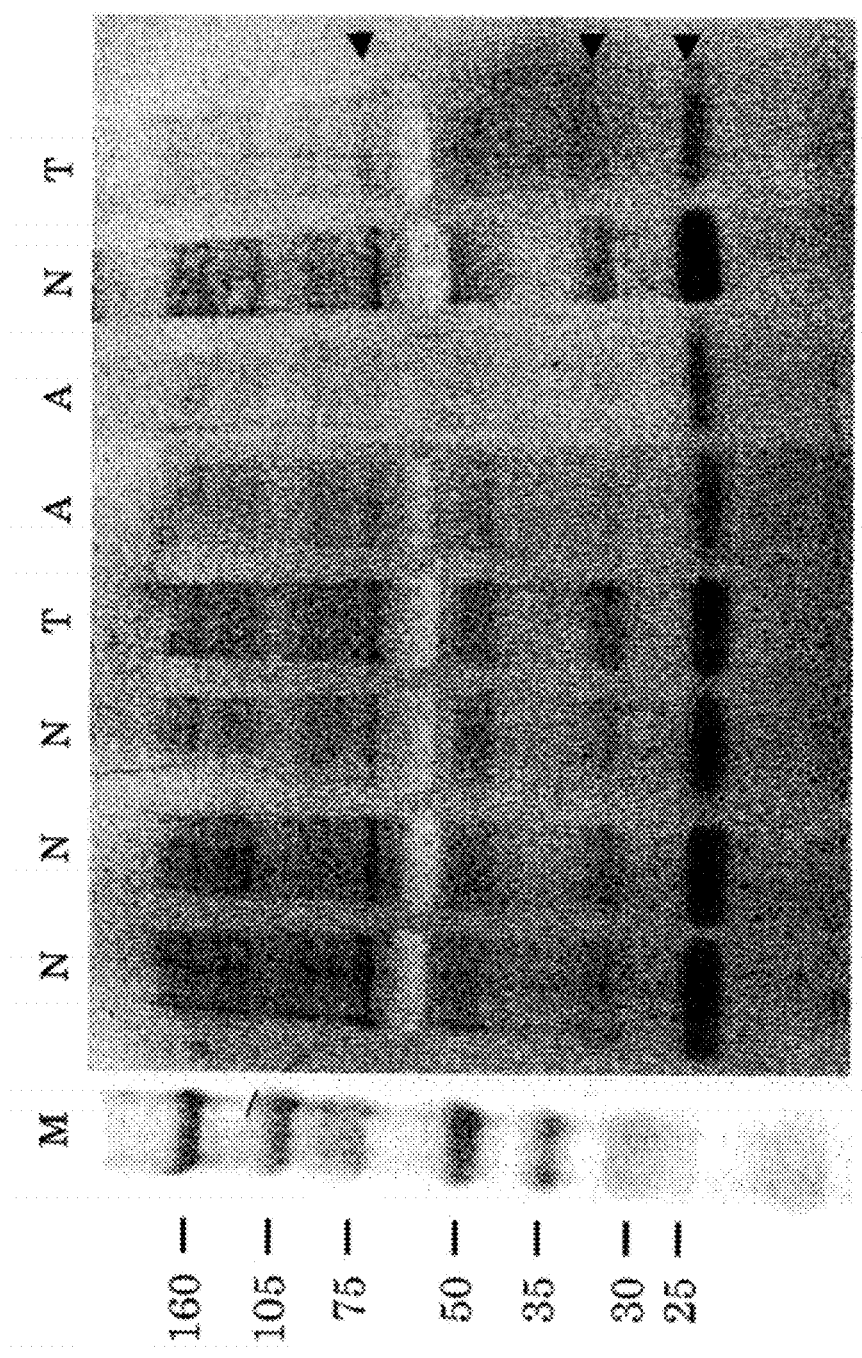
FIG. 3 shows cerebrospinal fluid WGA binding glycoprotein via lectin blotting with cerebrospinal WGA, with M representing the marker, N representing a sample derived from a non-dementia case, A representing a sample derived from an Alzheimer's disease case, T representing a sample derived from a tauopathy case, an upper-most arrow representing an approximately 75 kDa glycoprotein a, a middle arrow representing a glycoprotein around 30 to 33 kDa, and a lower-most arrow representing a glycoprotein of approximately 25 kDa.

The cerebrospinal fluid sample was heat-treated for five minutes in boiling water bath, along with the sample buffer (60 mM Tris-HCL, 25% glycerol, 2% SDS, 14.4 mM 2-ME, and 0.1% BPB). A 5% to 20% gradient gel was employed in electrophoresis, and the sample was applied and then electrophoresed in an electrophoresis buffer (25 mM Tris-HCl, 192 mM glycine, and 0.1% SDS). After electrophoresis was completed, the protein in the gel was electrically blotted on a PVDF membrane. The membrane was immersed in a blocking liquid for blocking, then incubated overnight with 20 mg/ml of the biotin labeled WGA for the detection of sugar chains, and linked to the sugar chains. Next, alkaline phosphotase labeled streptavidin (1:1000) was reacted for two hours at room temperature, and the WGA linked glycoprotein was detected using a BCIP/NBT chromogenic substrate. A representative detection target is illustrated in FIG. 3. In the figure, M represents a marker, N represents a sample derived from a non-dementia case, A represents a sample derived from an Alzheimer's disease case, and T represents a sample derived from a tauopathy case. The numerals on the left-hand side of the figure each respectively illustrate the molecular weight of the protein used in the marker. The units employed therein are kilodaltons (kDa). Moreover, in the figure, the upper-most arrow represents an approximately 75 kDa glycoprotein a, the middle arrow represents a glycoprotein of around 30 to 33 kDa, and the lower-most arrow represents a glycoprotein of approximately 25 kDa.

WGA binding glycoprotein variations were seen between samples derived from Alzheimer's disease cases and samples from other cases, and it was thought that some abnormality exists in the gylcosylation mechanism with regard to the proteins in the cerebrospinal fluid of patients with Alzheimer's disease. The proteins with reduced levels of WGA binding in the vicinity of approximately 75 kDa (a), 30 to 33 kDa, and approximately 25 kDa were detected in Alzheimer's case derived samples. As a result of this, it is thought that measuring the glycosylation of various proteins, including the below-indicated proteins, would lead to a novel diagnostic method for Alzheimer's disease.

Example 2

Comparison of Amount of WGA Binding Glycoprotein (Approximately 75 kDa Glycoprotein a) in Cerebrospinal Fluid From the results of Example 1, the quantitative changes in the most significantly changed approximately 75 kDa glycoprotein a were focused on, and a comparison of the amount of this 75 kDa glycoprotein was made between Alzheimer's disease cases, normal cases, and tauopathy cases.

Figure 4:
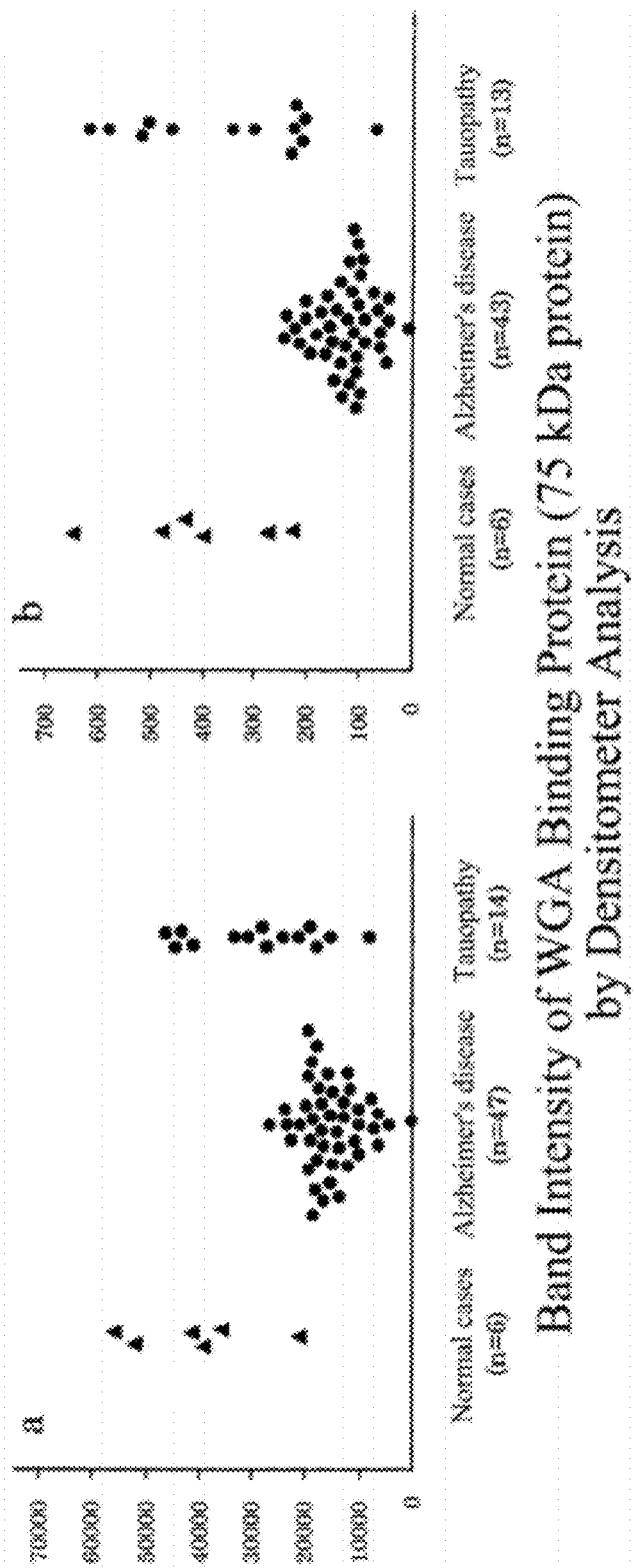
FIG. 4 shows two graphs quantifying a band of a WGA binding 75 kDa glycoprotein a obtained by the lectin blotting of FIG. 3, with graph (a) representing a graph of a band density as quantified, and graph (b) representing graph of a band density after being standardized by the amount of phosphorylated tau protein (pS199)

An investigation was conducted via an analysis of a lectin blot image obtained from experimental test similar that of Example 1. After the results of the lectin blotting were inputted into a computer, the density of the band was quantified using quantitative software (densitometer), and graphs were plotted. The resulting graphs are illustrated in FIG. 4. In FIG. 4, graph (a) is a graph of a band density quantified as is, and graph (b) is a graph of a band density after being standardized by the amount of phosphorylated tau protein (pS199). The measurement of the phosphorylated tau protein was conducted using a human phosphorylated tau protein ELISA kit (manufactured by BioSource International, Incorporated).

The glycoprotein of approximately 75 kDa was significantly reduced in Alzheimer's disease cases, and the detectable sensitivity and specificity of being identified alone in Alzheimer's disease were 74.6%, and 76.6%, respectively. Thus, it is even possible to differentiate between a tauopathy that would have been conventionally difficult for an indicator such as the phosphorylated tau protein, and the like, to differentiate from. Moreover, it is thought that since this reduction was even observed in patients in the early stages of Alzheimer's disease it may specifically contribute to the discovery/diagnosis of the early stages of AD.

Moreover, upon investigation of the ratio of phosphorylated tau protein with respect to this glycoprotein as an indicator, a significantly lower value was shown in Alzheimer's disease ($p<0.001$), and thus it was possible to detect Alzheimer's disease at a cutoff value of 184, with 85.1% sensitivity and 80.6% specificity. In addition, a comparison between tauopathy and Alzheimer's disease at a cutoff value of 205 showed 89.4% sensitivity and 92.3% specificity, and thus it was found to be an effective protein even in the differentiation between a tauopathy.

Example 3

Identification of an Approximately 75 kDa Glycoprotein a in Cerebrospinal Fluid

The identification of an approximately 75 kDa glycoprotein a showing significant quantitative changes was performed in the below-mentioned manner.

A 75 kDa glycoprotein was excised from a post-electrophoresis gel, and then digested with trypsin to create a peptide fragment. In the identification, a MALDI-TOF mass spectrometer was employed, and the mass of each peptide was measured by matrix-assisted laser desorption ionization (MALDI) and time-of-flight (TOF) MS analysis. In addition, amino acid analysis of the peptide was conducted, a pre-existing database (PMF: peptide mass fingerprint) was referenced using MASCOT database search software on the peptide mass and amino acid sequence, and it was identified.

The results of the abovementioned identification showed that the approximately 75 kDa glycoprotein a was transferrin. Moreover, this was also confirmed by western blotting using an anti-transferrin antibody.

Example 4

Quantification of Amount of Transferrin in Cerebrospinal Fluid

Since it is thought that the decreased amount of WGA binding shown by transferrin detected with WGA is due to either a reduction in transferrin itself or a variation in WGA binding sugar chains, studies for measuring the actual amount of transferrin were conducted.

The measurement of the amount of transferrin employed a human transferrin ELISA kit (manufactured by Bethyl Laboratories, Incorporated). The results thereof are indicated in Table 2.

TABLE 2

Cerebrospinal fluid transferrin levels

|  | Number of patients | Transferrin μg/ml |
|---|---|---|
| Alzheimer's disease | 40 | 24.6 ± 10.6 |
| Tauopathy | 10 | 22.8 ± 8.2 |
| Non-dementia comparison group | 29 | 25.0 ± 12.5 |

A significant difference was found even among the Alzheimer's disease group, tauopathy group, and non-dementia comparison group, respectively. It was clear that the decreased level of transferrin detected with WGA was due to variations in the sugar chains required for binding to WGA, and not variations in the amount of transferrin itself.

Example 5

Analysis of Transferrin Sugar Chains in Cerebrospinal Fluid

In order to analyze transferrin sugar chains, an investigation using mannose specific binding LCA was conducted. Since mannose is attached at the initial step of N-linked glycosylation, it was possible to conduct an investigation on the glycosylation capacity of sugar chains during the initial step by examining the existing state of mannose. It was presumed that the would be no difference in the amount of cerebrospinal fluid transferrin LCA binding between the Alzheimer's disease group and the control group, and that an abnormality in the sugar chains in the cerebrospinal fluid of a subject with Alzheimer's disease might be occurring after the step in which mannose is attached, specifically, it might be due to an abnormality in sialyation. Moreover, it was expected that transferrin sugar chain would be beneficial not only as a diagnostic marker, but also in the elucidation of the pathology of Alzheimer's disease by analyzing the glycosylation abnormality itself as unique pathological condition of Alzheimer's disease.

Example 6

Separation of Transferrin Isoforms

In order to provide a more detailed analysis of transferrin sugar chains, isoelectric focusing was conducted in the below-mentioned manner, and a transferrin having sugar chains with a varying number of sialic acids was separated.

Figure 5:
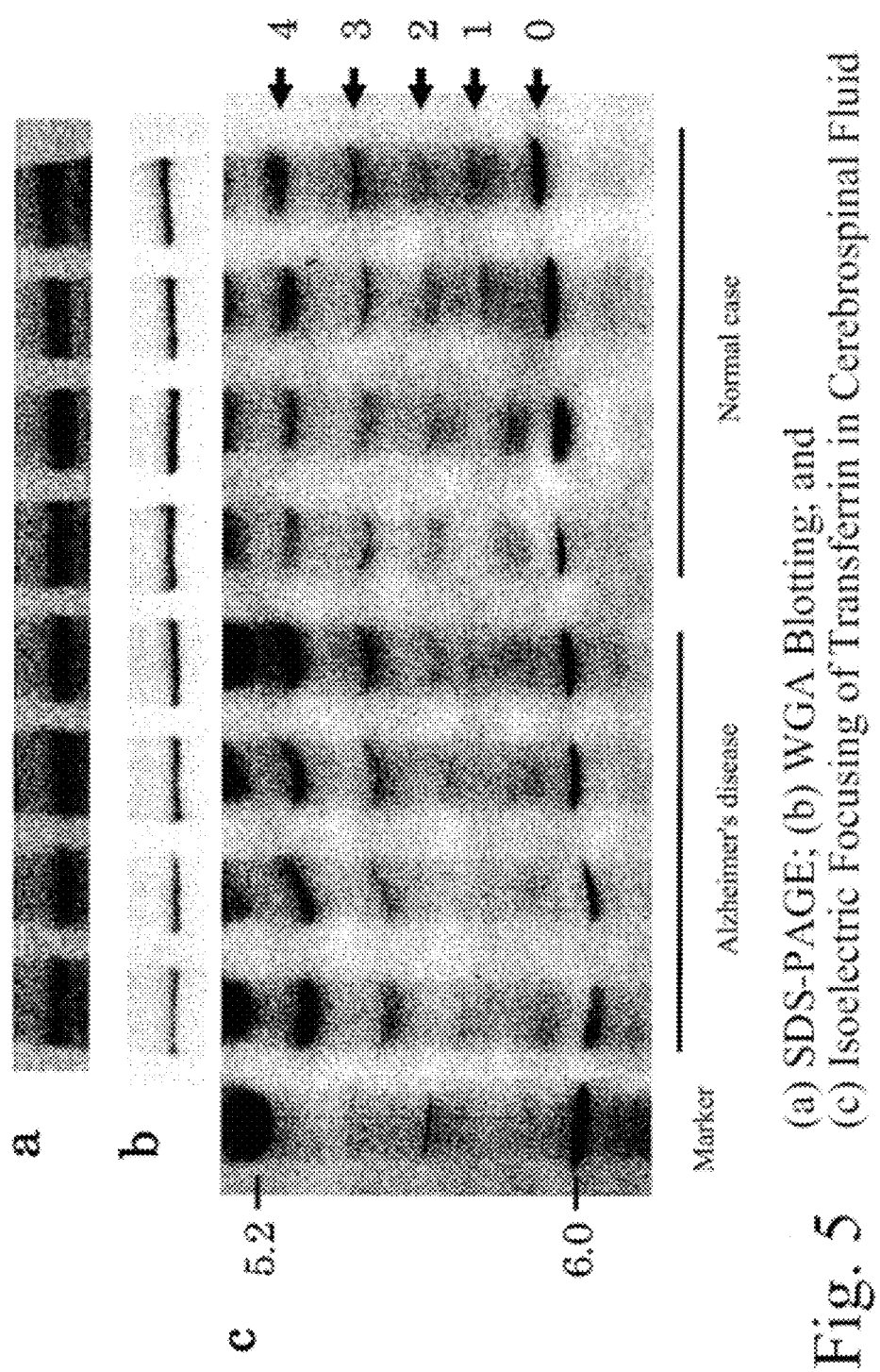
FIG. 5 shows the results of an analysis via transferrin isoelectric focusing, with (a) representing a diagram of the amount of post-SDS-PAGE transferrin detected by western blotting, (b) representing a diagram of 75 kDa glycoprotein a detected by lectin blotting using WGA, (c) representing a diagram of each isoform of transferrin separated by isoelectric focusing, and the right-hand sided numerals 0 to 4 representing the number of sialic acids in a sugar chain attached to each transferrin isoform.

A sample (cerebrospinal fluid) saturated with iron ions was employed in the isoelectric focusing of transferrin. The electrophoresis gel included an amphoteric carrier adjusted so as to allow separation at a pH of 4 to 6.5, and polyacrylamide gel (5% T, 3% C) was employed, so that the iron-saturated transferrin was separated based on an isoelectric point thereof. After the completion of isoelectric focusing, the amphoteric carrier was removed from the gel, then stain with Coomassie brilliant blue, and the protein (transferrin) was detected. The results thereof are illustrated in FIG. 5. In the figure, (a) represents a diagram of the amount of post-SDS-PAGE transferrin detected by western blotting, (b) represents a diagram of transferrin (approximately 75 kDa glycoprotein a) detected by lectin blotting using WGA, and (c) represents a diagram of each isoform of transferrin separated by isoelectric focusing. In diagram (c), the right-hand sided numerals 0 to 4 represent the number of sialic acids in a sugar chain attached to each transferrin isoform.

It was clear that transferrin sugar chains were different in Alzheimer's disease and other tauopathies. Specifically, in the Example, a reduction in sugar chains with one or two sialic acid attached thereto in Alzheimer's disease, and an increase in sugar chains with three or four sialic acid attached thereto were observed. Moreover, it was clear this leads to a reduction in WGA binding. It is thought because of this, transferrin having one or two sialic acids attached thereto, and transferrin having three or four sialic acids attached thereto may be employed as an indicator of the pathological state of Alzheimer's disease.

Example 7

Comparison of Amount SSA Binding Glycoprotein in Cerebrospinal Fluid

SSA was employed in place of WGA as the lectin via a similar technique to that of Example 1, and lectin blot analysis of a 75 kDa glycoprotein equivalent to transferrin was conducted. Then, the results of lectin blotting were quantified via a technique similar to that of Example 2, and then standardized by the weight of transferrin determined via the method of Example 3 to obtain the results shown in Table 3.

TABLE 3

|  | Number of patients | Amount of sialic acid (nmol/mg Tf) |  |
|---|---|---|---|
| AD | 26 | 20.82 ± 2.63 | $P < 0.01$ |
| Non-dementia group | 11 | 17.78 ± 2.20 |  |

Measurement of cerebrospinal fluid transferrin sugar chains via SSA . . . These are consistent with the results of isoelectric focusing In spite of the overall reduction in WGA binding among the transferrins (approximately 75 kDa glycoprotein) of the Alzheimer's disease group, there was a significant increase in SSA binding (transferrin having sialic acids attached thereto), and thus the significance of transferrin glycosylation in cerebrospinal fluid, specifically, the significance of sialic acid in a sugar chain thereof was confirmed.

From the abovementioned results, with regard to transferrin in cerebrospinal fluid, it is clear that employing transferrin having a sugar chain with a specific number of sialic acids attached thereto as an indicator allows for the differential diagnosis of Alzheimer's disease.

Example 8

Quantification of the Amount of Transferrin in Blood

With regard to the 27 cases of Alzheimer's disease and the 17 cases of non-dementia from the clinical cases employed as the subjects of Examples 1 to 7, the blood samples that were collected and prepared from the subjects via conventional method were subjected to the below-mentioned analysis.

Figure 6:
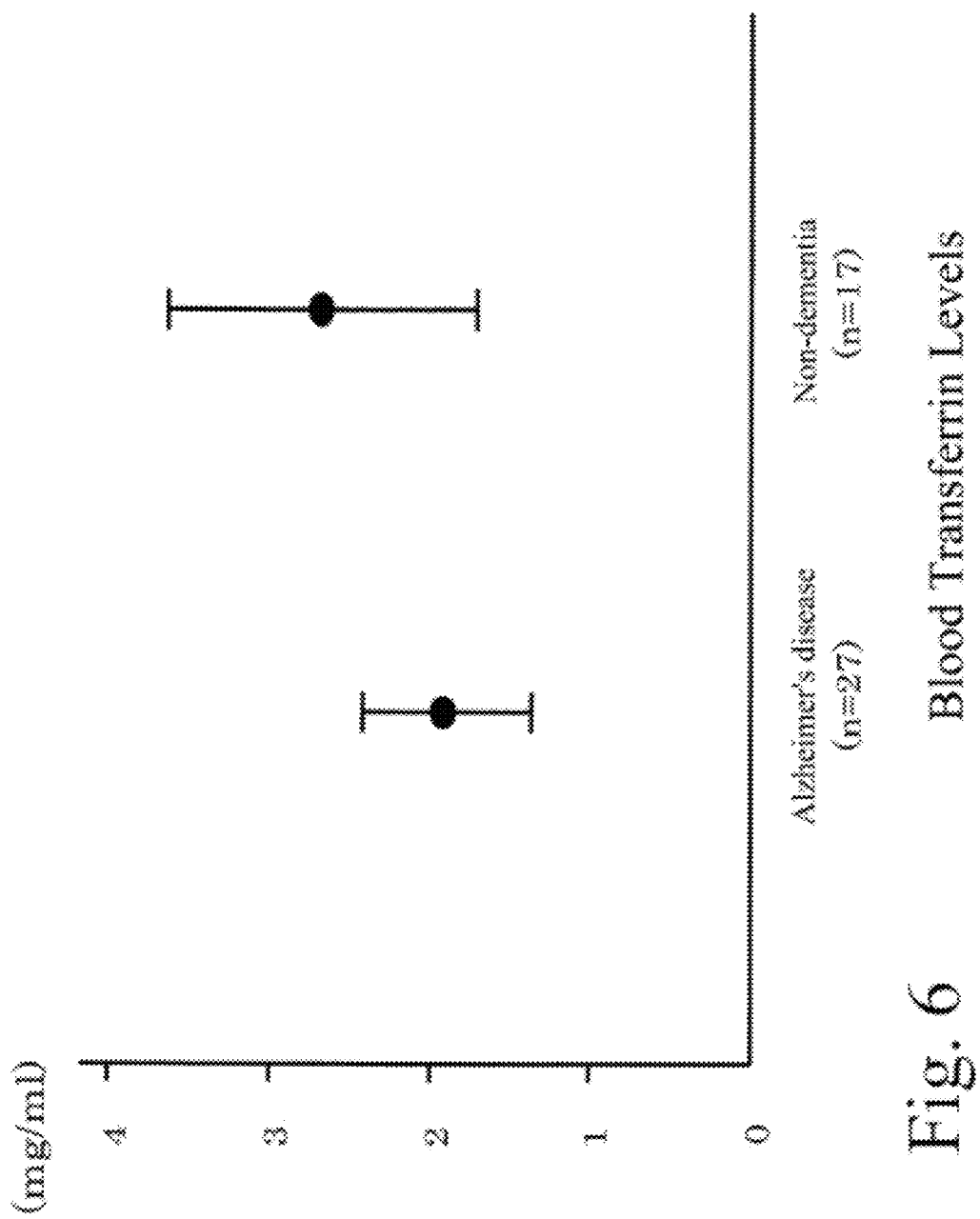
FIG. 6 is a graph quantifying transferrin in the blood.

Finally, measurements of transferrin in blood were conducted with a similar technique to that of Example 4. A graph of the results is shown in FIG. 6.

When comparing the non-dementia comparison group with the Alzheimer's group, the amount of transferrin in blood from the Alzheimer's disease group was significantly reduced (p<0.05). Thus, it was clear that the amount of transferrin in the blood is significantly reduced in Alzheimer's disease.

Example 9

Figure 7:
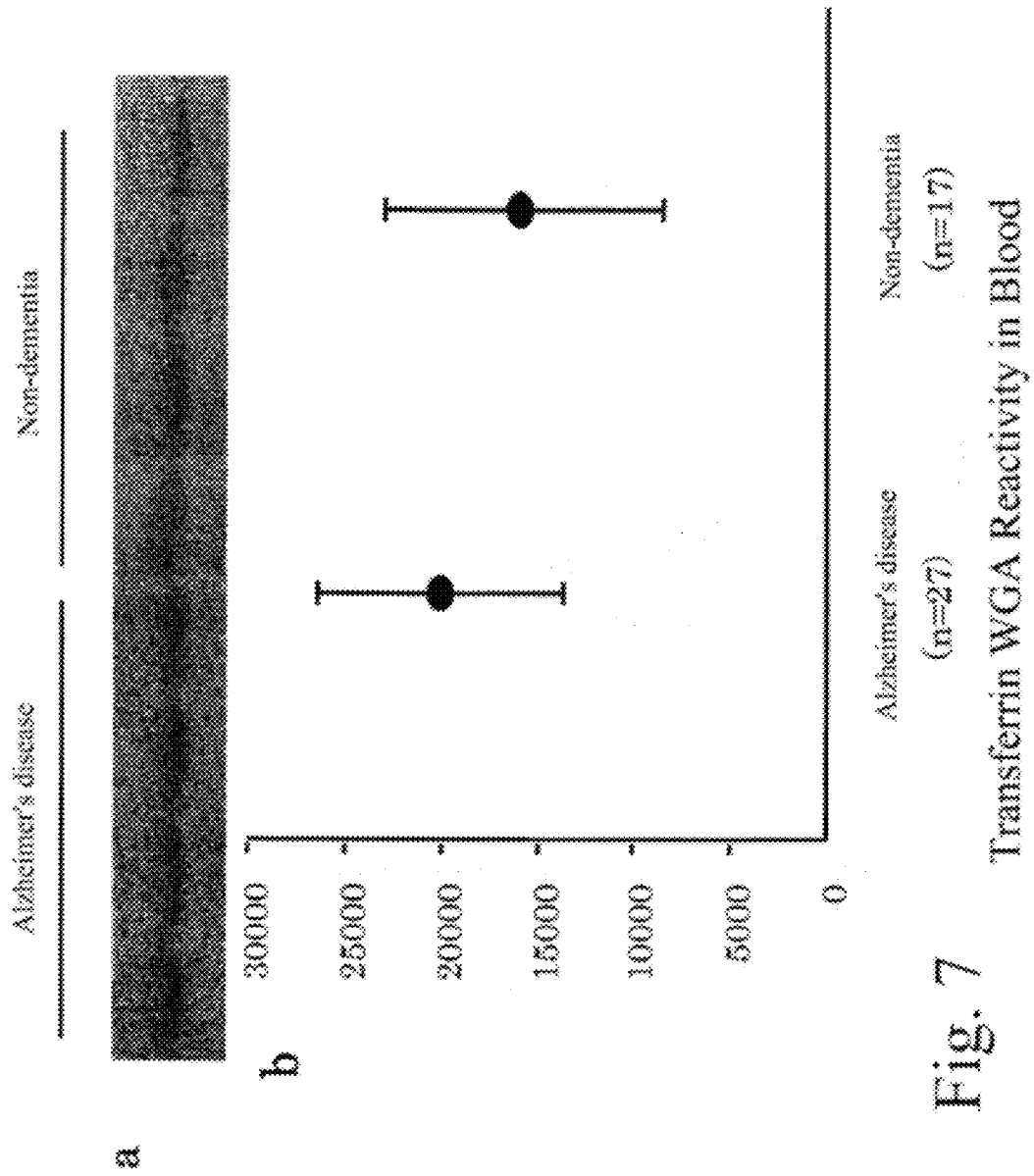
FIG. 7 is a diagram regarding the WGA binding transferrin (75 kDa protein) obtained by lectin blotting using blood WGA, with (a) representing a diagram of a band of the WGA binding transferrin (75 kDa protein) obtained by lectin blotting using blood WGA, and (b) is a graph quantifying such a band.

Comparison of Amount WGA Glycoprotein (Approximately 75 kDa Glycoprotein: Transferrin) in Blood Lectin blot analysis of the approximately 75 kDa glycoprotein equivalent to transferrin was conducted with a technique similar to that of Example 1, and then the results of the lectin blotting were quantified with a technique similar to that of Example 2. A graph of the results is illustrated in FIG. 7.

The results differed from those of the study using cerebrospinal fluid of Example 2, and there was a significant increase in WGA binding transferrin in blood from the Alzheimer's disease group as compared to that of the non-dementia group.

Figure 8:
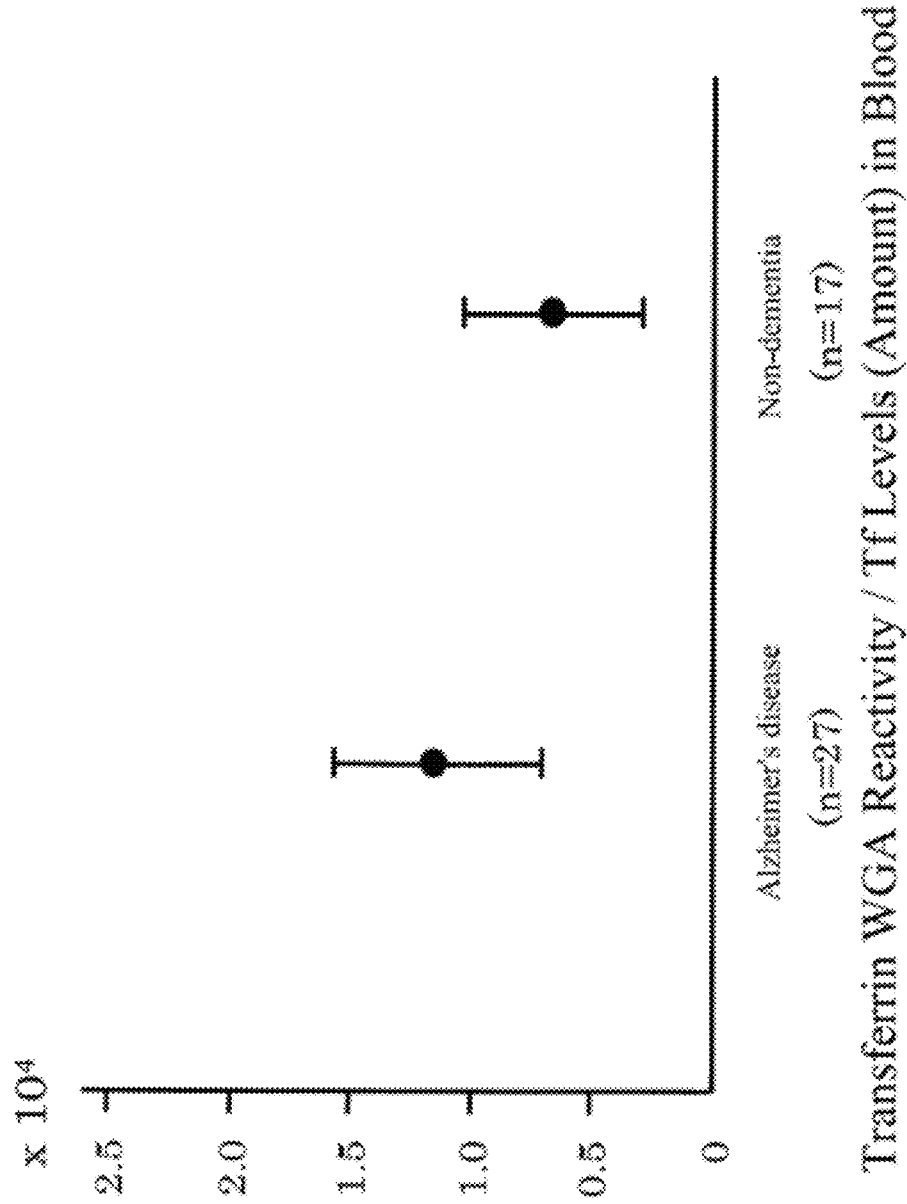
FIG. 8 is a graph standardizing the blood WGA binding transferrin shown in FIG. 7 with the amount of transferrin indicated in FIG. 6.

Moreover, because a significant variation was seen in both the amount of WGA binding transferrin in blood and the amount of transferrin in blood, a numerical value standardized by the ratio thereof was calculated, and graph of the results is indicated in FIG. 8. In an indicator (quantitative ratio) in which both the amount of transferrin in blood and the amount of WGA binding transferrin in blood were totaled, an even more significant difference was observed between the non-dementia group and Alzheimer's disease group.

Based the abovementioned results, with regard to the transferrin in the blood, it was clear that using an indicator totaling the overall amount of transferrin and the amount of transferrin having a sugar chain attached thereto, for example, such as that represented by WGA binding, allows for the diagnosis of Alzheimer's disease.

The abovementioned present invention was explained with reference to the Examples. However, these are merely Examples, and thus it should be understood that various modifications thereof are also possible, and that it would be obvious to one who is skilled in the art that such modifications would also be included within the scope of the present invention.

INDUSTRIAL APPLICABILITY

As mentioned above, the diagnostic kit, diagnostic marker, and a detection method for an indicator of the pathological state of the present invention are useful as a diagnostic kit, a diagnostic marker, and a detection method for a pathological indicator having a correlation to Alzheimer's disease.

The invention claimed is:

1. A diagnostic kit for diagnosing Alzheimer's disease comprising a detection means for quantitatively detecting transferrin having a sugar chain with a varying number of sialic acids attached thereto, and
   showing a quantitative ratio of transferrin having a sugar chain with one or two sialic acids attached thereto and transferrin having a sugar chain with three sialic acids attached thereto in a cerebrospinal fluid sample obtained from a mammal, as an indicator of the pathological state of Alzheimer's disease.

2. A diagnostic kit for diagnosing Alzheimer's disease comprising a detection means for quantitatively detecting transferrin having a sugar chain with a varying number sialic acids attached thereto, and
   showing either a decreased amount of transferrin having a sugar chain with one or two sialic acids attached thereto, or an increased amount of transferrin having a sugar chain with four sialic acids attached thereto, in a cerebrospinal fluid sample obtained from a mammal, with respect to cerebrospinal fluid obtained from a normal mammal of the same species, as an indicator of the pathological state of Alzheimer's disease.

3. A diagnostic kit for diagnosing Alzheimer's disease comprising a detection means for quantitatively detecting transferrin, and a detection means for quantitatively detecting transferrin having a sugar chain attached thereto, and
   showing an indicator obtained by totaling an amount of transferrin, and an amount of transferrin having a sugar chain attached thereto, in a blood sample obtained from a mammal, as an indicator of the pathological state of Alzheimer's disease.

4. The diagnostic kit according to claim 3, wherein the sugar chain is a WGA or SSA binding sugar chain.

5. The diagnostic kit according to claim 3, wherein the indicator is a quantitative ratio of transferrin and transferrin having a sugar chain attached thereto.

6. A diagnostic kit for diagnosing Alzheimer's disease comprising a detection means for quantitatively detecting transferrin, a detection means for quantitatively detecting transferrin having a sugar chain attached thereto, and a detection means for quantitatively detecting transferrin having a sugar chain with a varying number sialic acids attached thereto, and
   showing an indicator obtained by totaling an amount of transferrin in a blood sample obtained from a mammal, an amount of transferrin having a sugar chain attached thereto in the blood sample, and an amount of transferrin having a sugar chain with one or two sialic acids and/or transferrin having a sugar chain with three or four sialic acids in a cerebrospinal fluid sample obtained from a mammal, as an indicator of the pathological state of Alzheimer's disease.

7. The diagnostic kit according to any one of claims 1 to 6, wherein the detection means comprises lectin for lectin affinity electrophoresis.

8. The diagnostic kit according to any one of claims 1 to 6, wherein the detection means comprises a lectin for lectin blot analysis or a sugar chain recognizing antibody for western blot analysis.

9. The diagnostic kit according to any one of claims 1 to 6, wherein the detection means comprises a lectin for a lectin enzyme-linked immunosorbent assay, or a sugar chain recognizing antibody for an enzyme-linked immunosorbent assay.

10. The diagnostic kit according to any one of claims 1 to 6, wherein the detection means comprises a lectin array chip or an antibody array chip using a sugar chain recognizing antibody.

11. The diagnostic kit according to claim 8, wherein the lectin is WGA or SSA.

12. The diagnostic kit according to claim 8, wherein the sugar chain recognizing antibody is a sialic acid recognizing antibody.

13. The diagnostic kit according to claim 8, wherein the sugar chain recognizing antibody is an antibody recognizing transferrin having a sugar chain attached thereto.

14. A diagnostic marker for diagnosing Alzheimer's disease comprising a quantitative ratio of a transferrin having a sugar chain with one or two sialic acids attached thereto, and a transferrin having a sugar chain with three or four sialic acids attached thereto.

15. A diagnostic marker for diagnosing Alzheimer's disease comprising a decreased amount of transferrin having a sugar chain with one or two sialic acids attached thereto, or an increased amount of transferrin having a sugar chain with four sialic acids attached thereto in a cerebrospinal fluid sample obtained from a mammal, with respect to cerebrospinal fluid obtained from a normal mammal of the same species.

16. A diagnostic marker for diagnosing Alzheimer's disease comprising an indicator obtained by totaling an amount of transferrin and an amount of transferrin having a sugar chain attached thereto, in a blood sample.

17. A detection method of an indicator of the pathological state of Alzheimer's disease comprising steps of:
   quantitatively detecting transferrin having a sugar chain with a varying number of sialic acids attached thereto, and
   calculating a quantitative ratio of transferrin having a sugar chain with one or two sialic acids with respect to transferrin having a sugar chain with three or four sialic acids, for a cerebrospinal fluid sample obtained from a mammal.

18. A detection method of an indicator of the pathological state of Alzheimer's disease comprising steps of:
   quantitatively detecting transferrin having a sugar chain with a varying number of sialic acids attached thereto, for a cerebrospinal fluid sample obtained from a mammal, and
   calculating a decreased amount of transferrin having a sugar chain with one or two sialic acids, or an increased amount of transferrin having a sugar chain with four sialic acids, with respect to cerebrospinal fluid obtained from a normal mammal of the same species.

19. A detection method of an indicator of the pathological state of Alzheimer's disease comprising steps of:
   quantitatively detecting transferrin,
   quantitatively detecting transferrin having a sugar chain attached thereto, and
   calculating an indicator totaling the amount of transferrin, and the amount of transferrin having a sugar chain attached thereto,
   for a blood sample obtained from a mammal.

* * * * *

UNITED STATES PATENT AND TRADEMARK OFFICE
CERTIFICATE OF CORRECTION

| | |
|---|---|
| PATENT NO. | : 8,105,839 B2 |
| APPLICATION NO. | : 12/440094 |
| DATED | : January 31, 2012 |
| INVENTOR(S) | : Urakami et al. |

It is certified that error appears in the above-identified patent and that said Letters Patent is hereby corrected as shown below:

In Column 35, Claim 17, line 18, please delete "or four".

Signed and Sealed this
Twenty-eighth Day of August, 2012

David J. Kappos
*Director of the United States Patent and Trademark Office*